US012029392B2

(12) United States Patent
Chu

(10) Patent No.: US 12,029,392 B2
(45) Date of Patent: Jul. 9, 2024

(54) MEDICAL DEVICE INCLUDING A MEDICAL DEVICE MANAGEMENT SYSTEM

(71) Applicant: BOSTON SCIENTIFIC SCIMED, INC., Maple Grove, MN (US)

(72) Inventor: Michael S H Chu, Brookline, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 80 days.

(21) Appl. No.: 17/685,236

(22) Filed: Mar. 2, 2022

(65) Prior Publication Data

US 2022/0280021 A1    Sep. 8, 2022

Related U.S. Application Data

(60) Provisional application No. 63/155,955, filed on Mar. 3, 2021.

(51) Int. Cl.
*A61B 1/005* (2006.01)
(52) U.S. Cl.
CPC .......... *A61B 1/0052* (2013.01); *A61B 1/0057* (2013.01)
(58) Field of Classification Search
CPC ..... A61B 1/0052; A61B 1/0057; A61B 18/26; A61B 18/24; A61B 2018/00166; A61B 2018/00196; A61B 2018/00202; A61B 2018/00511; A61B 2018/0091; A61B 2018/00916; A61B 2018/00982; A61B 1/00048; A61B 1/00133; A61B 1/018; A61B 2017/00296; A61B 2017/00367; A61B 2017/00477; A61B 17/221; A61B 1/00137
See application file for complete search history.

(56) References Cited

U.S. PATENT DOCUMENTS

| 7,789,825 B2 | 9/2010 | Nobis et al. |
| 8,007,432 B2 | 8/2011 | Vakharia et al. |
| 9,095,686 B2 | 8/2015 | Zanne et al. |
| 9,433,340 B2 | 9/2016 | Jones et al. |
| 10,667,673 B2 | 6/2020 | Su et al. |

(Continued)

FOREIGN PATENT DOCUMENTS

JP    H09492 A    1/1997

OTHER PUBLICATIONS

International Search Report and Written Opinion dated Jun. 10, 2022 for International Application No. PCT/US2022/018561.

*Primary Examiner* — Aaron B Fairchild
(74) *Attorney, Agent, or Firm* — Seager, Tufte & Wickhem, LLP

(57) ABSTRACT

An actuation mechanism for an endoscope is disclosed. The actuation mechanism includes a housing configured to be attached to a handle of the endoscope and a thumbwheel coupled to the housing. Rotation of the thumbwheel causes longitudinal translation of an elongated medical device through a working channel of the endoscope. In some instances, the actuation mechanism includes a drive wheel and/or a roller wheel, wherein the elongate medical device is compressively positioned between the roller wheel and/or the drive wheel. Rotation of the thumbwheel may cause the drive wheel and/or the roller wheel to rotation in opposite rotational directions.

14 Claims, 20 Drawing Sheets

(56) References Cited

U.S. PATENT DOCUMENTS

| | | | |
|---|---|---|---|
| 2005/0267327 A1* | 12/2005 | Iizuka | A61B 1/00133 |
| | | | 600/106 |
| 2007/0225754 A1 | 9/2007 | Measamer et al. | |
| 2016/0324399 A1 | 11/2016 | Banju et al. | |
| 2017/0143195 A1 | 5/2017 | Yee et al. | |
| 2017/0215901 A1* | 8/2017 | Harrah | A61B 17/221 |
| 2019/0021707 A1 | 1/2019 | Belsky et al. | |
| 2019/0029498 A1 | 1/2019 | Mankowski et al. | |
| 2019/0232027 A1 | 8/2019 | Chu | |
| 2019/0246876 A1* | 8/2019 | Schaning | A61B 18/1815 |
| 2019/0380562 A1* | 12/2019 | Deuel | A61B 1/00131 |
| 2021/0045619 A1* | 2/2021 | Sauer, Md | A61B 1/313 |
| 2022/0296078 A1* | 9/2022 | Suzuki | A61B 1/005 |

\* cited by examiner

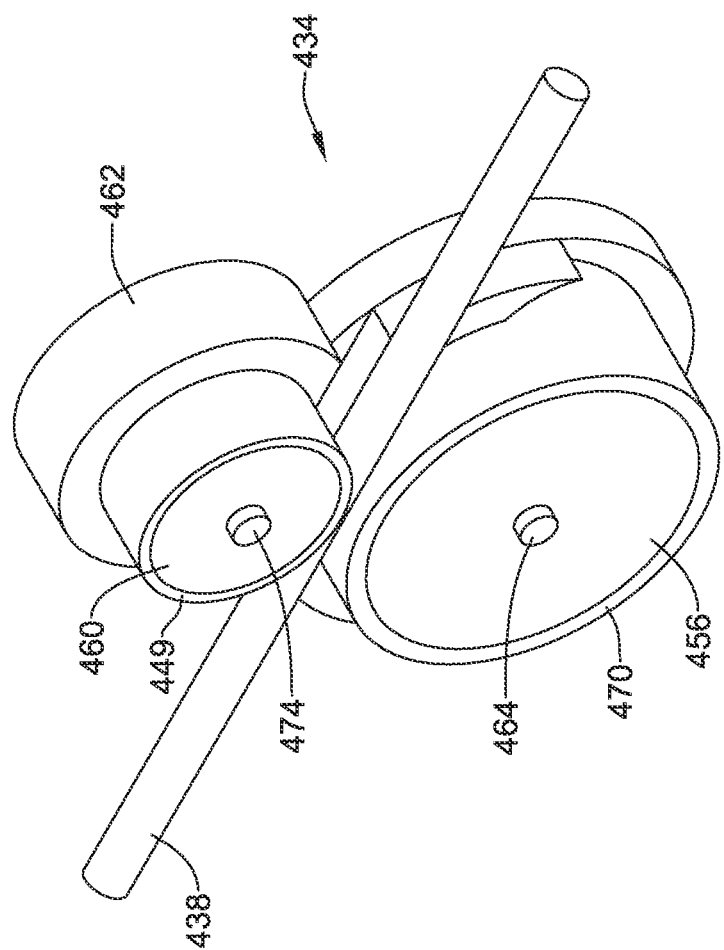

MEDICAL DEVICE INCLUDING A MEDICAL DEVICE MANAGEMENT SYSTEM

CROSS REFERENCE TO RELATED APPLICATIONS

This application claims the benefit of and priority to U.S. Provisional Patent Application Ser. No. 63/155,955 filed on Mar. 3, 2021, the disclosure of which is incorporated herein by reference.

TECHNICAL FIELD

The present disclosure pertains to medical devices, and methods for manufacturing medical devices. More particularly, the present disclosure pertains to a medical device including an ergonomic medical device management system for elongated devices used in conjunction with the medical device.

BACKGROUND

Flexible ureteroscopes are utilized in the examination and treatment of kidneys and may generally include features which improve treatment site accessibility and patient comfort. Flexible ureteroscopes may be provided with a flexible tip section that is controlled by a physician via manipulation of various components attached to the scope's handle. Such manipulation enables the physician to maneuver the tip of the scope to different locations within the body (e.g., different locations within the kidney). Additionally, ureteroscopes are typically used in conjunction with other medical devices during a medical procedure. For example, urologists may use a flexible ureteroscope in combination with both a laser fiber and a retrieval device (e.g., retrieval basket) to both pulverize kidney stones and remove the pulverized debris from the body. Accordingly, these procedures may require not only manipulating various features of the ureteroscope to control the tip of the scope, but also to introduce and manipulate ancillary devices used in conjunction with the ureteroscope.

Manipulating both the ureteroscope and the ancillary devices may require an assistant to exchange the one or more elongated devices while the physician manipulates the handle of the ureteroscope. This exchange may be time consuming and may cause accidental droppage or damage to the elongated devices, adding additional time and cost to the procedure. Therefore, it may be desirable to design a handle of a ureteroscope, or other endoscopic device, in which the physician may be able to manipulate the tip of the elongate shaft of the endoscope with one hand, while also being able to manipulate additional devices with the same hand. Medical devices including a handle having a device management system which allows a user to manipulate the handle in addition to additional ancillary devices are disclosed herein.

BRIEF SUMMARY

This disclosure provides design, material, manufacturing method, and use alternatives for medical devices.

An example is an actuation mechanism for an endoscope. The actuation mechanism includes a housing configured to be attached to a handle of an endoscope and a first thumbwheel coupled to the housing. Rotation of the first thumbwheel causes longitudinal translation of a first elongated medical device through a working channel of the endoscope.

Alternatively or additionally to any of the embodiments above, the actuation mechanism further includes a first drive wheel coupled to the housing. The first thumbwheel engages the first drive wheel such that rotation of the first thumbwheel causes rotation of the first drive wheel.

Alternatively or additionally to any of the embodiments above, the actuation mechanism further includes a first roller wheel coupled to the housing. An outer circumferential surface of the first roller wheel is positioned adjacent to an outer circumferential surface of the first drive wheel such that the first elongated medical device may be positioned between the outer circumferential surface of the first roller wheel and the outer circumferential surface of the first drive wheel. Rotation of the first thumbwheel causes rotation of the first drive wheel to move the first elongated medical device through the working channel of the endoscope.

Alternatively or additionally to any of the embodiments above, the first roller wheel and the first drive wheel are configured to cooperatively exert a compressive force on the first elongated medical device to frictionally engage the first elongated medical device therebetween.

Alternatively or additionally to any of the embodiments above, the first thumbwheel includes a circumferential surface, and wherein a band of material extends around each of the first thumbwheel, the first drive wheel and the first roller wheel.

Alternatively or additionally to any of the embodiments above, the housing includes an inner housing and an outer housing, wherein the first thumbwheel, the first drive wheel and the first roller wheel are positioned between the inner housing and the outer housing.

Alternatively or additionally to any of the embodiments above, the actuation mechanism further includes a second thumbwheel coupled to the housing, a second drive wheel coupled to the housing and a second roller wheel coupled to the housing. The second thumbwheel engages the second drive wheel such that rotation of the second thumbwheel causes longitudinal translation of a second elongated medical device through a working channel of the endoscope.

Alternatively or additionally to any of the embodiments above, the first thumbwheel includes a first diameter and the first drive wheel includes a second diameter, and wherein the second diameter is less than the first diameter.

Alternatively or additionally to any of the embodiments above, the actuation mechanism further includes a first roller wheel coupled to the housing, wherein an outer circumferential surface of the first roller wheel is positioned adjacent to an outer circumferential surface of the first thumbwheel such that the first elongated medical device may be positioned between the outer circumferential surface of the first roller wheel and the outer circumferential surface of the first thumbwheel, and wherein rotation of the first thumbwheel causes rotation of the first roller wheel to move the first elongated medical device through the working channel of the endoscope.

Alternatively or additionally to any of the embodiments above, the housing includes a channel extending from an outer surface of the housing into a portion of a wall of the housing, wherein the channel is configured to accept a proximal end of a tubular member of the first elongated medical device, and wherein the proximal end of the tubular member of the first elongated medical device is fixedly attached to the channel.

Alternatively or additionally to any of the embodiments above, the channel is configured to accept an elongate member of the first elongated medical device extending within a lumen of the tubular member of the first elongated medical device.

Alternatively or additionally to any of the embodiments above, the actuation mechanism further includes a rotation cap coupled to the housing. A proximal end of the elongate member is attached to the rotation cap such that rotation of the rotation cap moves the elongate member within the lumen of the tubular member of the first elongated medical device.

Another example is an endoscopic medical device. The endoscopic medical device includes a handle having a proximal end region and a distal end region, an elongate shaft coupled to the distal end region of the handle and extending distally therefrom, and an actuation assembly coupled to the proximal end region of the handle. The actuation assembly includes a housing, a first thumbwheel coupled to the housing, and a second thumbwheel coupled to the housing. Rotation of the first thumbwheel causes a first elongated medical device to translate through the elongate shaft. Rotation of the second thumbwheel causes a second medical device to translate through of the elongate shaft.

Alternatively or additionally to any of the embodiments above, the rotation of the first thumbwheel to translate the first medical device occurs independently of the rotation of the second thumbwheel to translate the second medical device.

Alternatively or additionally to any of the embodiments above, the actuation assembly further includes a first drive wheel and a first roller wheel coupled to the housing. The first drive wheel is configured to be rotated by the first thumbwheel. The actuation assembly further includes and a second drive wheel and a second roller wheel coupled to the housing. The second drive wheel is configured to be rotated by the second thumbwheel. The first drive wheel and the first roller wheel are configured to cooperatively exert a force on the first medical device positioned therebetween. The second drive wheel and the second roller wheel are configured to cooperatively exert a force on the second medical device positioned therebetween.

Alternatively or additionally to any of the embodiments above, rotation of the first thumbwheel rotates the first drive wheel and the first roller wheel in opposite rotational directions to translate the first elongated medical device through the elongate shaft, and wherein rotation of the second thumbwheel rotates the second drive wheel and the second roller wheel in opposite rotational directions to translate the second elongated medical device through the elongate shaft.

Alternatively or additionally to any of the embodiments above, the first thumbwheel includes a first diameter and the first drive wheel includes a second diameter, and wherein the second diameter is less than the first diameter.

Another example is an actuation assembly for an endoscope. The actuation assembly includes a housing configured to be attached to a handle of an endoscope, a thumbwheel coupled to the housing, and a rotation cap coupled to the housing. Rotation of the thumbwheel causes translation of a first elongated shaft within a working channel of the endoscope. The rotation cap is coupled to a second elongated shaft extending within a lumen of the first elongated shaft. Rotation of the rotation cap causes movement of the second elongated shaft within the lumen of the first elongated shaft.

Alternatively or additionally to any of the embodiments above, the rotation of the thumbwheel causes both the first elongated shaft and the second elongated shaft to move together within the working channel of the endoscope.

Alternatively or additionally to any of the embodiments above, the rotation cap is actuatable between a retracted position and an extended position, wherein the rotation cap is biased toward the retracted position.

Alternatively or additionally to any of the embodiments above, the actuation assembly further includes a drive wheel. The drive wheel has a circumferential surface in contact with both the thumbwheel and the first elongated shaft.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 18A is a perspective view of another configuration of a shaft advancement mechanism.

Figure 1:
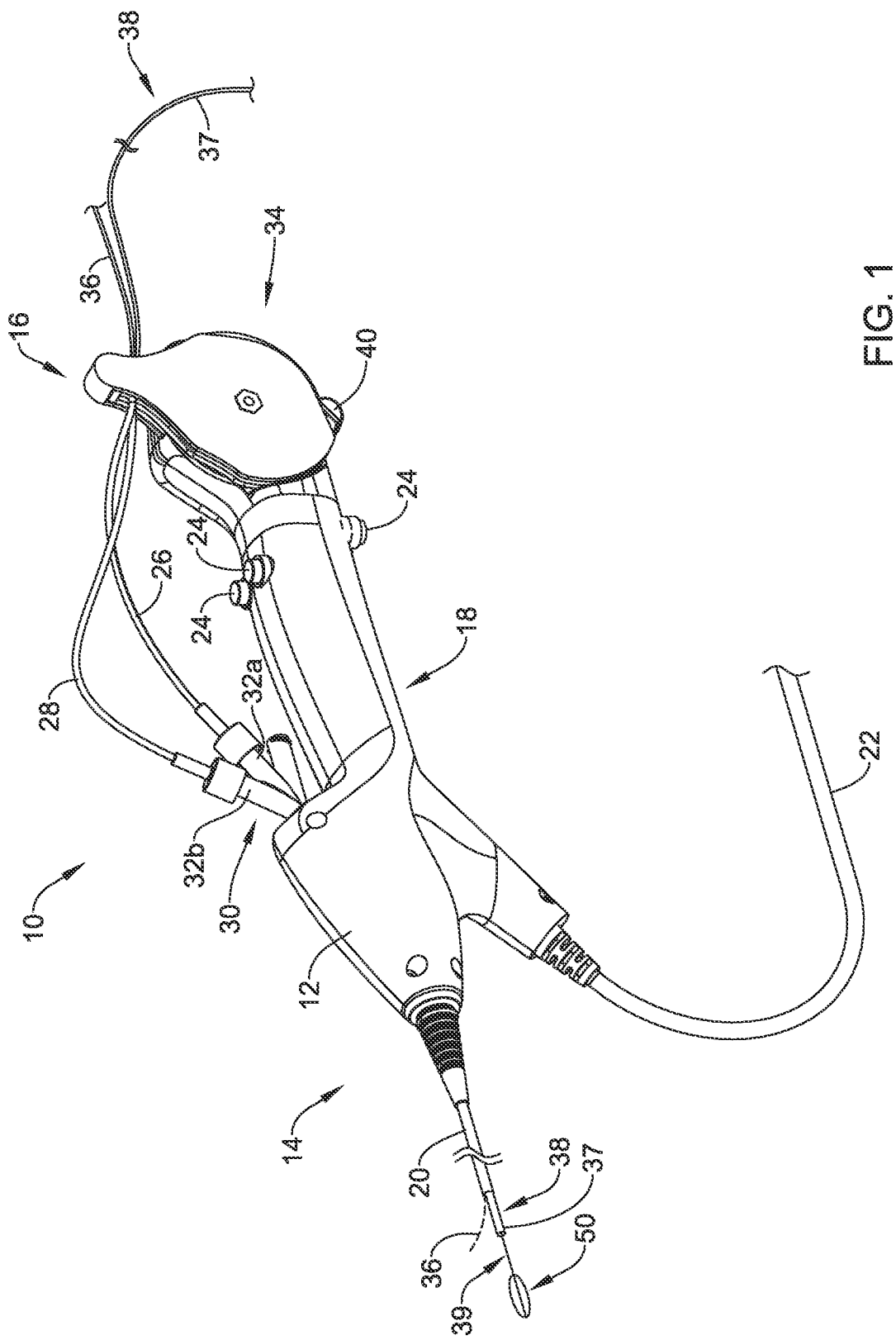
FIG. 1 is a perspective view of an example medical device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the current disclosure. Those skilled in the art will recognize that the various elements described and/or shown may be arranged in various combinations and configurations without departing from the scope of the disclosure. The detailed description and drawings illustrate example embodiments of the current disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed example(s). Each instance of the features may include and/or be encompassed by the singular disclosure(s), unless expressly stated to the contrary. For simplicity and clarity purposes, not all elements of the current disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

As discussed above, the present disclosure relates to medical devices having a handle which may be designed to manipulate the distal end of a scope shaft as well as other medical devices used in conjunction with the scope. For example, the medical device may include a ureteroscope having a handle, whereby the handle includes a manual medical device advancement system. In these examples, the medical device advancement system may include one or more drive wheels capable of being manipulated with only a single thumb of the physician.

FIG. 1 is a perspective view of an example medical device 10. The medical device 10, shown as an endoscope, may be any of a number of different types of medical devices utilized in a variety of medical interventions. For example, the particular type of medical device 10 may be identified by the particular anatomy desired to be reached. For example, the medical device 10 may be a ureteroscope (e.g., Litho-Vue™ scope), bronchoscope, hysteroscope, cystoscope, colonoscope, duodenoscope, esophagoscope, or any other type of related endoscope. The medical device 10 may include a handle 12 having a distal end 14, a proximal end 16 and a medial region 18 positioned between the distal end 14 and the proximal end 16. It is noted that the terms "proximal" and "distal", as used herein, are intended to refer to a direction toward (proximal) and away from (distal) a user of the device (e.g., physician). Further, the medical device 10 may include an elongate shaft 20 extending distally from the handle 12. In general, the elongate shaft 20 may take the form of a polymer or metal tube. In some embodiments, the elongate shaft 20 may be constructed with a reinforcing braid, liner, web, weave, etc.

The elongate shaft 20 may include a lumen defining a working channel extending through the shaft 20 from a distal end region of the shaft 20 to an access port 30 (e.g., Y-connector) that may be engaged with the handle 12 or another portion of the medical device 10. Although the elongate shaft 20 is described as having a single working channel in FIG. 1, it can be appreciated that in other embodiments, the medical device 10 may include multiple working channels, as desired.

Further, the handle 12 may include a deflection knob 40 or other actuator, which may be used to control movement (e.g., deflection) of the distal tip of the shaft 20 during operation. For example, the deflection knob 40 may control up and down movement or deflection of the distal tip of the shaft 20. In some instances, the deflection knob may be a self-locking or friction lock type knob which maintains the knob (and the elongate shaft 20) at its deflected position after being released. The handle 12 may also include one or a plurality of buttons 24, which may be used to activate suction or deliver fluid such as air, saline and/or water, etc. through a lumen of the medical device 10 or perform other functions as desired. These are just examples. Other variations and/or features for medical device 10 are contemplated.

In some embodiments, a cable 22 extends from the handle 12 and is configured for attachment to an electronic device (not pictured) such as e.g. a computer system, a console, a microcontroller, etc. for providing power, analyzing endoscopic data, controlling the endoscopic intervention, or performing other functions. In some embodiments, the electronic device to which the cable 22 is connected may have functionality for recognizing and exchanging data with other endoscopic accessories.

As discussed above, FIG. 1 illustrates that the handle 12 of the endoscope may be utilized in conjunction with additional medical devices during a medical procedure. For example, the medical device 10 may be a ureteroscope (e.g., flexible ureteroscope) utilized in the pulverization and removal of renal stones (e.g., kidney stones). Accordingly, in some examples, the handle 12 may be utilized in conjunction with a laser fiber 36 utilized to break up the renal stone and a retrieval device (e.g., retrieval basket) utilized to remove the renal stone pieces. Further, the handle 12 (and various components thereof) may be utilized to not only manipulate the elongate shaft 20, but may also be utilized to manipulate a laser fiber 36 and/or a retrieval device 38 which may extend though both portions of the handle 12 and the shaft 20. While the following disclosure may generally describe the medical device 10 as being used with a laser fiber 36 and/or a retrieval device 38, it can be appreciated that the medical device 10 (and components thereof) may be used with any elongated medical devices including sheaths, tubular members, guidewires, lasers, or the like.

FIG. 1 further illustrates that the laser fiber 36 may pass through the first hub 32a of the access port 30, continue through the distal end 14 of the handle 12 and pass into the working channel of the elongate shaft 20. After passing through the length of the working channel of the elongate shaft 20, the laser fiber 36 may exit the distal end of the elongate shaft 20 (not shown in FIG. 1).

FIG. 1 illustrates a retrieval device 38 entering a shaft advancement device 34 which is coupled to the proximal end region 16 of the handle 12. The retrieval device 38 may include a tubular shaft 37 having a lumen extending from its distal end to its proximal end. After passing through the shaft advancement device 34, the retrieval device 38 may enter the lumen of a first connection tube 26 (it is noted that the proximal end of the first connection tube 26 may be fixedly attached to the shaft advancement device 34). The retrieval device 38 may continue passing through the lumen of the first connection tube 26 into a first hub 32a of an access port 30. While FIG. 1 illustrates the access port 30 including three hubs, it can be appreciated that the access port 30 may include more of less than three hubs. For example, the access port 30 may include 1, 2, 3, 4, 5, 6 or more hubs.

Additionally, the access port 30 may include a variety of different geometric shapes that may include one or more hubs configured to connect to one or more connection tubes. Further, in some examples, the access port 30 may be eliminated from the handle 12. In these examples, the handle housing, itself, may include one or more hubs extending directly from the outer surface of the handle housing. These hubs may be utilized to attach directly to one or more connection tubes.

FIG. 1 further illustrates that the retrieval device 38 may pass through the first hub 32a of the access port 30, continue through the distal end 14 of the handle 12 and pass into the working channel of the elongate shaft 20, or an additional working channel of the elongate shaft 20. After passing through the length of the working channel of the elongate shaft 20, the retrieval device 38 may exit the distal end of the elongate shaft 20, as shown in FIG. 1.

FIG. 1 further illustrates that, in some examples, the retrieval device 38 may include an end effector, such as a retrieval basket 50, for manipulation and/or grasping particulates, such as renal stone fragments. The retrieval device 38 may include a retrieval wire 39 extending within the lumen of the tubular shaft 37 of the retrieval device 38 for manipulating the end effector, such as the retrieval basket 50. For example, FIG. 1 illustrates that, in some examples, a retrieval wire 39 may enter the lumen of the tubular shaft 37 of the retrieval device 38 at its proximal end, pass through the lumen of the tubular shaft 37 of the retrieval device 38 (and consequently, through the first connection tube 26, the first hub 32a, the distal end 14 of the handle 12 and through the working channel of the elongate shaft 20) before exiting the distal end of the tubular shaft 37 of the retrieval device 38.

While FIG. 1 illustrates the retrieval wire 39 as including a retrieval basket 50, it can be appreciated that the retrieval wire 39 may include a variety of different end effectors that are utilized in conjunction with the retrieval device 38. For example, the retrieval wire 39 may include a retrieval net, forceps, an immobilization device, a stone sweeping device, or other similar medical devices.

It can be appreciated that, in some examples the retrieval basket 50 may shift from a first, unexpanded configuration to a second, expanded configuration by longitudinally actuating the retrieval wire 39 relative to the tubular member of the retrieval device 38. During use, the retrieval basket 50 may be utilized to capture a renal stone, or fragments thereof, when in the expanded configuration. After being captured in the retrieval basket 50, a clinician may remove the renal stone and/or fragments from the body by retracting the retrieval basket 50 proximally toward the distal end of the tubular shaft 37 of the retrieval device 38 to close the retrieval basket 50 around the renal stone and/or fragment. It can be appreciated that the renal stone and/or fragment may remain trapped in the retrieval basket 50 while remaining outside the lumen of the tubular member of the retrieval device 38. To remove the renal stone and/or fragment from the body, the clinician may withdraw the retrieval device 38 proximally through the working channel of the elongate shaft 20 of the medical device 10 from the patient's body.

Like that described with respect to the retrieval device 38, FIG. 1 illustrates a laser fiber 36 entering the shaft advancement device 34 which is coupled to the proximal end region 16 of the handle 12. After passing through the shaft advancement device 34, the laser fiber 36 may enter the lumen of a second connection tube 28 (it is noted that the proximal end of the second connection tube 28 may be fixedly attached to the shaft advancement device 34). The laser fiber 36 may continue passing through the lumen of the second connection tube 28 into a second hub 32b of the access port 30. It can be appreciated that FIG. 1 shows the retrieval device 38 extending out of the distal end of the elongate shaft 20 while the distal end of the laser fiber 36 is shown in dashed lines simply for illustrative purposes. Therefore, it can be appreciated that during a medical procedure, only one or the other of the laser fiber 36 or the retrieval device 38 (including the retrieval wire 39 positioned within the lumen of the tubular shaft 37 of the retrieval device 38) may occupy the working channel of the elongate shaft 20 while the other of the laser fiber 36 and the retrieval device 38 may be positioned proximal of the access port 30 within either of the first connection tube 26 or the second connection tube 28. In other instances, the laser fiber 36 may occupy a first working lumen of the elongate shaft 20 while the retrieval device 38, including the tubular shaft 37 of the retrieval device 38 and retrieval wire 39 extending therethrough, occupies the second working lumen of the elongate shaft 20. It can be appreciated that, in some examples, each of the first connection tube 26 and the second connection tube 28 may be transparent or translucent, thereby permitting a clinician to visualize the distal end of the laser fiber 36 or the distal end of the retrieval device 38 located therein when withdrawn from the working channel of the elongate shaft 20 to permit the other device to occupy the working channel of the elongate shaft 20. It may be desirable for a clinician to be able to visually confirm that the distal end of the retrieval device 38 or the distal end of the laser fiber 36 is located in either the first connection tube 26 or the second connection tube 28, respectively, when the other of the retrieval device 38 and the laser fiber 36 is advanced distally into the working channel of the elongate shaft 20.

For example, a medical procedure to remove a renal stone may include manipulation of the shaft advancement device 34 (described in greater detail below) to advance the laser fiber 36 into the second connection tube 28 such that the laser fiber 36 is positioned just proximal of the second hub 32b of the access port 30. As discussed above, the distal end of the laser fiber 36 may be visible within the transparent or translucent connection tube 28 when positioned proximal of the second hub 32b. Next, the shaft advancement device 34 may be utilized to advance the retrieval device 38 (including the tubular shaft 37 of the retrieval device 38 and the retrieval wire 39 disposed therein) into the first connection tube 26 such that the retrieval device 38 is positioned just proximal of the first hub 32a of the access port 30. As discussed above, the distal end of the retrieval device 38 may be visible within the transparent or translucent connection tube 26 when positioned proximal of the first hub 32a. In this configuration, each of the retrieval device 38 and the laser fiber 36 may be referred to as being "parked" in its respective connection tube 26/28 in order to permit the other to be advanced into the working channel of the elongate shaft 20.

An example next step in the procedure may include a physician manipulating the shaft advancement device 34 to advance the laser fiber 36 through the working channel of the elongate shaft 20 to the target site, whereby the laser fiber 36 may be utilized to pulverize the renal stone. Next, the physician may utilize the advancement device 34 to retract the laser fiber 36 proximally until the distal end of the laser fiber 36 is positioned proximal of the second hub 32b and back into the second connection tube 28. It can be appreciated that when the distal tip of the laser fiber 36 is seen through the transparent or translucent connection tube 28, the laser fiber 36 is cleared from the working channel of the elongate shaft 20. It can be appreciated that retracting the laser fiber 36 back into the second connection tube 28 may open up the working channel of the elongate shaft 20 to subsequently permit the retrieval device 38 to be advanced distally therethrough. Accordingly, a next step in the procedure may include a physician manipulating the shaft advancement device 34 to advance the retrieval device 38 distally through the working channel of the elongate shaft 20 to the target site, whereby the retrieval basket 50 may be deployed distal of the distal end of the elongate shaft 20 of the medical device 10 to capture the kidney stone and/or fragments.

As discussed above, the renal stone and/or fragments may remain trapped in the retrieval basket 50 while the clinician withdraws the retrieval device 38 and the elongate shaft 20 of the medical device 10 from the patient's body. The medical device 10 may thereafter be reinserted into the body to capture additional renal stones and/or fragments, if desired.

FIGS. 2-5B and the corresponding discussion below will describe the components and function of the shaft advancement device 34.

Figure 2:
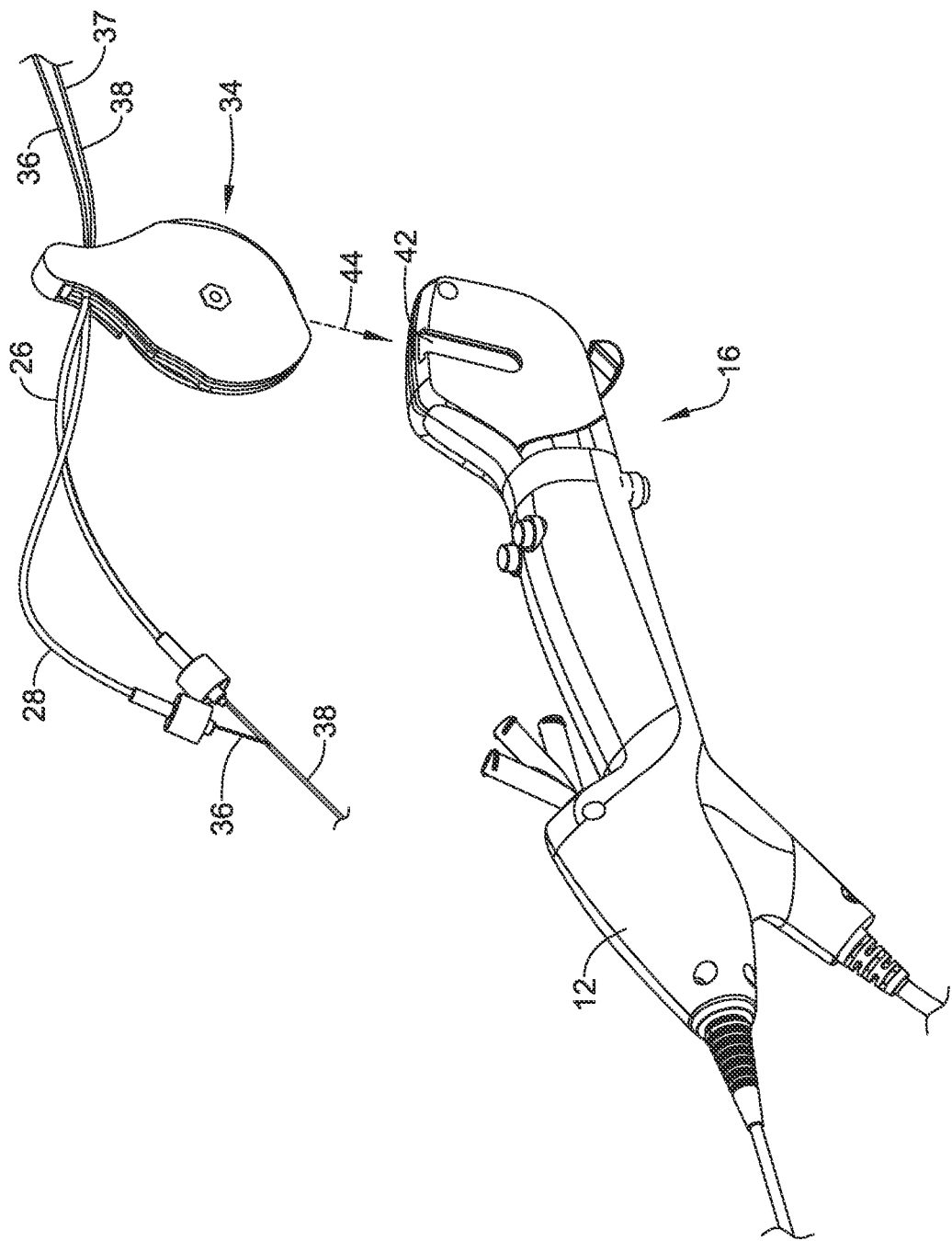
FIG. 2 is another perspective view of the example medical device shown in FIG. 1.

FIG. 2 illustrates that the shaft advancement device 34 may be removably coupled to the proximal end region 16 of the handle 12. In other instances, the shaft advancement device 34 may be coupled to the proximal end region 16 of the handle 12 in another manner. As described in FIG. 1, FIG. 2 illustrates the retrieval device 38 and the laser fiber 36 passing through the shaft advancement device 34 and through the first connection tube 26 and the second connection tube 28, respectively. While the shaft advancement device 34 has been described as being removably coupled to the handle 12, it is contemplated that, in some embodiments, the shaft advancement device 34 may be integrated with and/or fixedly attached to the handle 12 such that its removal from the handle 12 is not intended.

As shown in FIG. 2, the shaft advancement device 34 may be coupled to the handle 12 via insertion of an engagement feature of the shaft advancement device 34 into a slot 42 located in the proximal end region 16 of the handle 12. As will be shown in FIG. 3, the slot 42 may be designed to accept an axle (shown in FIG. 3) located on a housing component of the shaft advancement device 34. The insertion of the axle into the slot 42 of the handle 12 is depicted with the arrow 44 of FIG. 2. In other embodiments, the shaft advancement device 34 may include a different engagement feature (e.g., post, pin, fastener, etc.) configured to engage with the slot 42 of other engagement feature of the handle 12. It can be appreciated that the shaft advancement device 34 may be packaged as a separate device that is optionally coupled to the handle 12 when desired. For example, a physician may opt to attach the shaft advancement device 34 prior to procedures involving the manipulation of the handle 12 and additional medical devices such as the laser fiber 36 and the retrieval device 38. It can be appreciated that the physician may remove the shaft advancement device 34 from the handle 12 when desired.

Figure 3:
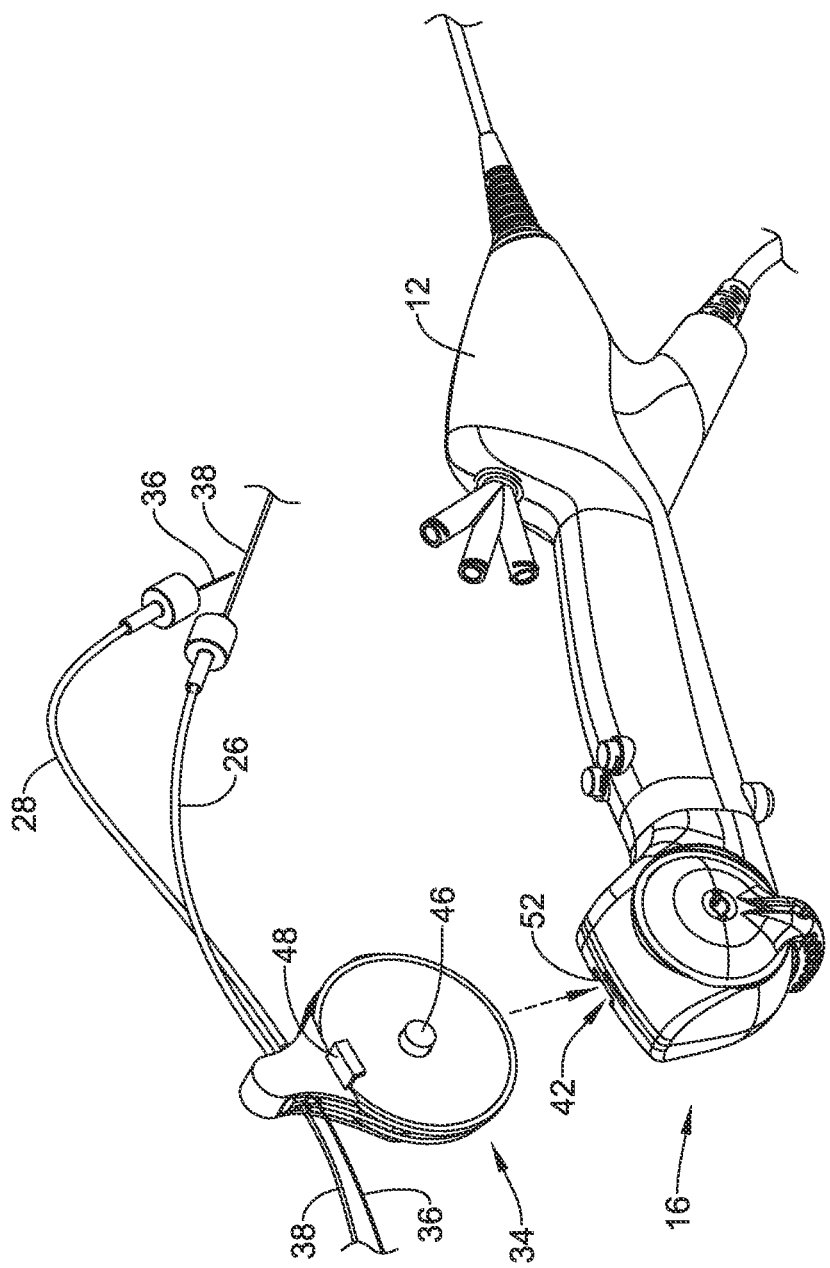
FIG. 3 is another perspective view of the example medical device shown in FIG. 1.

As discussed above, FIG. 3 illustrates the insertion of the axle 46 of the shaft advancement device 34 into a slot 42 of the handle 12. Additionally, FIG. 3 illustrates that the shaft advancement device 34 may further include a post (e.g., clip) 48 which is designed to be inserted into a recess 52 located along the distal end region 16 of the handle 12. It can be appreciated that the recess 52 may be positioned adjacent to the upper region of the slot 42.

It can be further appreciated that the engagement of the axle 46 within the slot 42, in combination with the insertion of the flat portion of the post or clip 48 into the recess 52, may limit rotation of the shaft advancement device 34 when coupled with the handle 12 in addition to providing a sufficient retention force such that the shaft advancement device 34 will not inadvertently separate from the handle 12 during a medical procedure. For example, the dimensions of the axle 46 and the post or clip 48 may be designed such that they provide a press fit or interlocking fit within the slot 42 and the recess 52, respectively.

Figure 4:
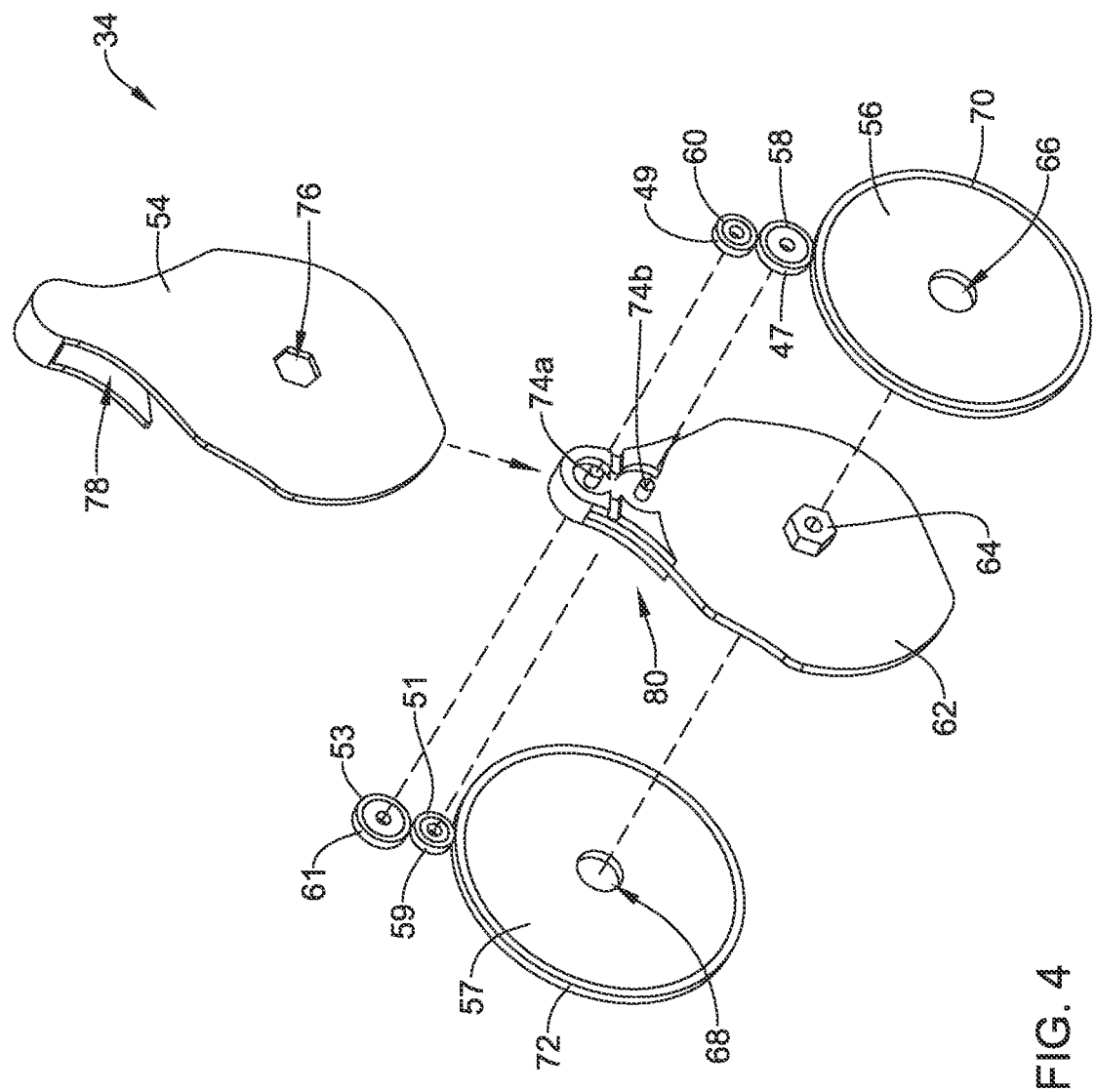
FIG. 4 is an exploded view of the components of a shaft advancement mechanism of the medical device shown in FIG. 3.

FIG. 4 illustrates an exploded view of the shaft advancement device 34 described above. For clarity, the first connection shaft 26, the second connection shaft 28, the laser fiber 36, and the retrieval device 38 have been omitted from FIG. 4.

FIG. 4 illustrates that shaft advancement device 34 may include a housing, including an inner housing 62 (e.g., first housing member) which may be positioned (e.g., "sandwiched") between a first thumbwheel 56 and a second thumbwheel 57, and an outer housing 54 (e.g., a second housing member). The first thumbwheel 56 may be coupled to the inner housing 62 via the extension of an axle 64 of the inner housing 62 through an aperture 66 of the first thumbwheel 56. FIG. 4 illustrates that the axle 64 of the inner housing 62 may be generally located in a central region of the inner housing 62. Further, FIG. 4 illustrates that the axle 64 may be generally shaped as a hexagon. However, while FIG. 4 shows the axle 64 including a hexagon shape in FIG. 4, it can be appreciated that the axle 64 may include a variety of shapes. For example, the axle 64 could include a cylindrical, triangular, polygonal, square, or other similar shapes.

Similarly, the second thumbwheel 57 may be coupled to the inner housing 62 via the extension of the axle 46 (not visible in FIG. 4, but shown in FIG. 3) of the inner housing 62 through an aperture 68 of the second thumbwheel 57. FIG. 4 illustrates that the axle 46 of the inner housing 62 may be generally located in a central region of the inner housing 62. It can be appreciated that the axle 46 may be axially aligned with the axle 64. Additionally, FIG. 4 illustrates that the axle 46 may be generally shaped as a cylinder. However, while FIG. 4 shows the axle 46 including a cylindrical shape in FIG. 4, it can be appreciated that the axle 46 may include a variety of shapes. For example, the axle 46 could include a hexagon, triangular, polygonal, square, or other similar shapes. Additionally, it can be appreciated that each of the first thumbwheel 56 and the second thumbwheel 57 may be press fit onto the axle 64 and the axle 46, respectively while allowing rotation of the first and second thumbwheels 56/57 relative thereto.

FIG. 4 further illustrates that each of the first thumbwheel 56 and the second thumbwheel 57 may include a band of material which extends circumferentially around the perimeter of each of the first thumbwheel 56 and the second thumbwheel 57. For example, the first thumbwheel 56 may include a band 70 of material that extends circumferentially around the perimeter of the first thumbwheel 56. Similarly, the second thumbwheel 57 may include a band 72 of material that extends circumferentially around the perimeter of the second thumbwheel 57. The material that is used to construct the band of material 70 and the band of material 72 may be designed too generally include materials which provide grip when a user is manipulating the first thumbwheel 56 and/or the second thumbwheel 57. For example, the band of material 70 and the band of material 72 may include rubber, silicone, nitrile butadiene rubber, thermoplastic elastomers, neoprene, or similar materials.

Additionally, in some examples, the band of material band 70 and the band of material 72 may include an elastic material. Utilization of an elastic material to construct the band of material 70 and the band of material 72 may be advantageous as an elastic material may be resistant to being removed from the first thumbwheel 56 and/or the second thumbwheel 57. In other words, an elastic material may provide a compressing force onto the outer circumferential surface of the first thumbwheel 56 and/or the second thumbwheel 57. Further, band of material 70 and the band of material 72 may include a roughened or textured surface that is suitable to be in contact with both other wheels and the thumb of a user.

When assembled, it can be appreciated that the first thumbwheel 56 and/or the second thumbwheel 57 may be rotated around the axles 64 and 46, respectively, in ether a clockwise or counterclockwise direction. Further, as will be described in greater detail below, a physician may use their thumb (or another finger) of their hand grasping the handle 12 of the medical device 10 to manually rotate the first thumbwheel 56 and/or the second thumbwheel 57. It can be appreciated that each of the first thumbwheel 56 and/or the second thumbwheel 57 may be rotated in either direction (e.g., each of the first thumbwheel 56 and/or the second thumbwheel 57 may be rotated in a clockwise direction or a counterclockwise direction).

FIG. 4 further illustrates that the shaft advancement device 34 may include a first drive wheel 58. The first drive wheel 58 may be coupled to the inner housing 62 via a pin 74b, which extends away from the surface of the inner housing 62. It can be appreciated that the first drive wheel 58 may rotate in a clockwise direction or a counterclockwise direction around the axis of the pin 74b. Additionally, FIG. 4 illustrates that the first drive wheel 58 may include a band of material 47 extending circumferentially around its perimeter. The circumferential surface of the first drive wheel 58 may be in direct contact with the circumferential surface of the first thumbwheel 56. The band of material 47 may be similar in form and function as the band of material 70 described above. Additionally, FIG. 4 illustrates that the first drive wheel 58 may be in contact with the first thumbwheel 56 (e.g., the band of material 70 of the first thumbwheel 56 may directly contact the band of material 47 of the first drive wheel 58).

FIG. 4 further illustrates that the shaft advancement device 34 may include a first roller wheel 60. The first roller wheel 60 may be coupled to the inner housing 62 via a pin 74a, which extends away from the surface of the inner housing 62. It can be appreciated that the first roller wheel 60 may rotate in a clockwise direction or a counterclockwise direction around the axis of the pin 74a. Additionally, FIG. 4 illustrates that the first roller wheel 60 may include a band of material 49 extending circumferentially around its perimeter. The band of material 49 may be similar in form and function as the band of material 70 described above. The circumferential surface of the first drive wheel 58 may be placed adjacent to the circumferential surface of the first roller wheel 60. For example, FIG. 4 illustrates that the first roller wheel 60 may be in contact with the first drive wheel 58 (e.g., the band of material 47 of the first drive wheel 58 may directly contact the band of material 49 of the first roller wheel 58), or a small gap may remain therebetween for placement of the tubular shaft 37 of the retrieval device 38 therebetween.

As will be described in greater detail below, because the first thumbwheel 56 directly contacts the first drive wheel 58, rotation of the first thumbwheel 56 will cause rotation of the first drive wheel 58 in a direction that is opposite to the rotation of the first thumbwheel 56. For example, clockwise rotation (as viewed from the outer surface of the thumbwheel 56) of the first thumbwheel 56 will cause a counterclockwise rotation of the first drive wheel 58. Similarly, because the first drive wheel 58 directly contacts the first roller wheel 60, rotation of the first drive wheel 58 will cause rotation of the first roller wheel 60 in a direction that is opposite to the rotation of the first drive wheel 58. For example, counterclockwise rotation of the first drive wheel 58 will cause a clockwise rotation of the first roller wheel 60. It can further be appreciated that the rotation of the first thumbwheel 56 results in the first roller wheel 60 being rotated in the same direction as the first thumbwheel 56 (while the first drive wheel 58 is rotated in an opposite direction to both the first thumbwheel 56 and the first roller wheel 60).

The first thumbwheel 56 may have a diameter greater than the diameter of the first drive wheel 58 to provide a mechanical advantage. For example, the diameter of the first thumbwheel 56 may be two times or more, three times or more, or four times or more of the diameter of the first drive wheel 58. Thus, one full revolution of the first thumbwheel 56 may result in greater than one full revolution of the first drive wheel 58. In some instances, the first thumbwheel 56 may be sized relative to the first drive wheel 58 in a 2:1 ratio, a 3:1 ratio, a 4:1 ratio, or a 5:1 ratio, for example.

FIG. 4 further illustrates that the shaft advancement device 34 may include a second drive wheel 59. The second drive wheel 59 may be coupled to the inner housing 62 via a pin (not visible in FIG. 4), which extends away from the surface of the inner housing 62. It can be appreciated that the second drive wheel 59 may rotate in a clockwise direction or a counterclockwise direction. Additionally, FIG. 4 illustrates that the second drive wheel 59 may include a band of material 51 extending circumferentially around its perimeter. The circumferential surface of the second drive wheel 59 may be in direct contact with the circumferential surface of the second thumbwheel 57. The band of material 51 may be similar in form and function as the band of material 72 described above. Additionally, FIG. 4 illustrates that the second drive wheel 59 may be in contact with the second thumbwheel 57 (e.g., the band of material 72 of the second thumbwheel 57 may directly contact the band of material 51 of the second drive wheel 59).

FIG. 4 further illustrates that the shaft advancement device 34 may include a second roller wheel 61. The second roller wheel 61 may be coupled to the inner housing 62 via a pin (not visible in FIG. 4), which extends away from the surface of the inner housing 62. It can be appreciated that the second roller wheel 61 may rotate in clockwise direction or a counterclockwise direction. Additionally, FIG. 4 illustrates that the second roller wheel 61 may include a band of material 53 extending circumferentially around its perimeter. The band of material 53 may be similar in form and function as the band of material 72 described above. The circumferential surface of the second drive wheel 59 may be placed adjacent to the circumferential surface of the second roller wheel 61. For example, FIG. 4 illustrates that the second roller wheel 61 may be in contact with the second drive wheel 59 (e.g., the band of material 51 of the second drive wheel 59 may directly contact the band of material 53 of the second roller wheel 61), or a small gap may remain therebetween for placement of the laser fiber 36 therebetween.

As will be described in greater detail below, because the second thumbwheel 57 directly contacts the second drive wheel 59, rotation of the second thumbwheel 57 will cause rotation of the second drive wheel 59 in a direction that is opposite to the rotation of the second thumbwheel 57. For example, counterclockwise rotation (as view from the outer surface of the second thumbwheel 57) of the second thumbwheel 57 will cause a clockwise rotation of the second drive wheel 59. Similarly, because the second drive wheel 59 directly contacts the second roller wheel 61, rotation of the second drive wheel 59 will cause rotation of the second roller wheel 61 in a direction that is opposite to the rotation of the second drive wheel 59. For example, clockwise rotation of the second drive wheel 59 will cause a counterclockwise rotation of the second roller wheel 61. It can be further appreciated that the rotation of the second thumbwheel 57 results in the second roller wheel 61 being rotated in the same direction as the second thumbwheel 57 (while the second drive wheel 59 is rotated in an opposite direction to both the second thumbwheel 57 and the second roller wheel 61).

The second thumbwheel 57 may have a diameter greater than the diameter of the second drive wheel 59 to provide a mechanical advantage. For example, the diameter of the second thumbwheel 57 may be two times or more, three times or more, or four times or more of the diameter of the second drive wheel 59. Thus, one full revolution of the second thumbwheel 57 may result in greater than one full revolution of the second drive wheel 59. In some instances, the second thumbwheel 57 may be sized relative to the second drive wheel 59 in a 2:1 ratio, a 3:1 ratio, a 4:1 ratio, or a 5:1 ratio, for example.

It can be appreciated one or more of the "wheels" described herein (including all the wheels described with respect to FIG. 4) do not necessarily have to directly contact one another to rotate one another. Rather, in some examples, one or more of the wheels may be connected via belts or chains, etc. to pulleys or gears, etc. attached to the wheels. For example, independent wheels may each include a gear whereby each gear of the two wheels are coupled to each other via a drive belt or drive chain. It can be appreciated that the rotation of one wheel will rotate the other wheel via the drive belt or drive chain connection. Further, gear ratios may be employed to tailor the speed/force of the drive wheels.

FIG. 4 further illustrates that the housing of the shaft advancement device 34 may include an outer housing 54. The outer housing 54 may be designed such that it covers a portion of the lateral (outer facing) surface of the first thumbwheel 56 without covering a corresponding lateral (outer facing) surface of the second thumbwheel 57. However, in other instances, the outer housing 54 may be designed to cover a lateral (outer facing) surface of the second thumbwheel 57, if desired. Further, FIG. 4 illustrates the outer housing 54 may include an aperture 76 through which the axle 64 may extend (e.g., the outer housing 54 may be attached to the inner housing 62 via engagement of the axle 64 through the aperture 76).

Additionally, the outer housing 54 may be positioned over a portion of the inner housing 62, the first thumbwheel 56, the first drive wheel 58, the first roller wheel 60, the second drive wheel 59 and the second roller wheel 61. Referring back to FIGS. 2-3, the outer housing 54 is shown positioned over a portion of the inner housing 62, the first thumbwheel 56, the first drive wheel 58, the first roller wheel 60, the second drive wheel 59 and the second roller wheel 61. Referring back to FIG. 2, the axle 64 is shown extending through the aperture 76 of the outer housing 54. It can be further appreciated that the outer housing 54 may include a channel 78 which is designed to accept the upper head portion 80 of the inner housing 62. The upper head portion 80 of the inner housing 62 may be defined as that portion of the inner housing 62 which includes the first drive wheel 58, the first roller wheel 60, the second drive wheel 59 and the second roller wheel 61. It can be appreciated from FIGS. 2-3, that, when assembled, the outer housing 54 may cover the first drive wheel 58, the first roller wheel 60, the second drive wheel 59 and the second roller wheel 61 while permitting a user to access and rotate the first thumbwheel 56 and the second thumbwheel 57.

Figure 5A:
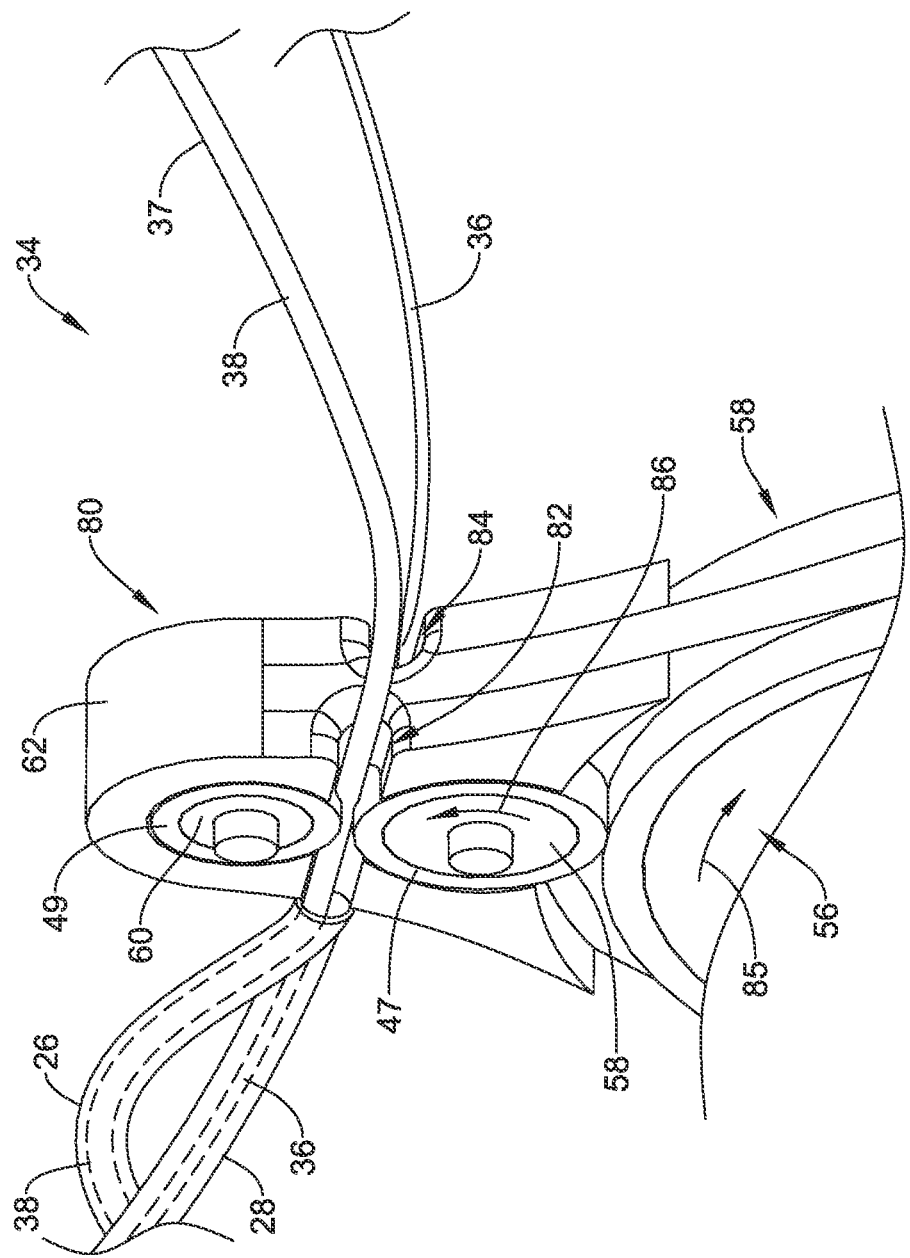
FIG. 5A is a detailed view of the shaft advancement mechanism of the medical device shown in FIG. 1.

FIG. 5A illustrates a detailed view of the shaft advancement device 34 (for clarity, the outer housing 54 has been omitted from FIG. 5A). In particular, FIG. 5A illustrates the upper head portion 80 of the inner housing 62 which includes the first drive wheel 58, the first roller wheel 60, the second drive wheel 59 (not visible in FIG. 5A, but shown in FIG. 5B) and the second roller wheel 61 (not visible in FIG. 5A, but shown in FIG. 5B). Additionally, FIG. 5A illustrates that first drive wheel 58 in direct contact with the first thumbwheel 56.

Additionally, FIG. 5A illustrates the laser fiber 36 extending through an opening 84 formed in the inner housing 62 and the retrieval device 38 extending through an opening 82 formed in the inner housing 62 (it can be appreciated from the above discussion that the retrieval wire 39 may extend through the tubular shaft 37 of the retrieval device 38 but is not visible in FIG. 5A). Further, FIG. 5A illustrates the tubular shaft 37 of the retrieval device 38 may be sandwiched (i.e., pressed) between the first drive wheel 58 and the first roller wheel 60 (e.g., between the band of material 47 of first drive wheel 58 and the band of material 49 of the first roller wheel 60).

FIG. 5A further illustrates the proximal end of the first connection tube 26 may be fixedly attached to the housing, such as the inner housing 62. For example, the proximal end of the first connection tube 26 may be adhesively attached to the inner housing 62. Other attachment methods are contemplated to fixedly attach the proximal end of the first connection tube 26 to the housing (e.g., the inner housing 62). For example, the proximal end of the first connection tube 26 may be flared while the housing 62 may include a projection designed to engage and mate with the flared portion of the first connection tube 26. In other examples, the proximal end of the first connection tube 26 may be expanded over a barb fitting of the housing 62. Additionally, FIG. 5A illustrates that after passing between the first drive wheel 58 and the first roller wheel 60, the retrieval device 38, or other elongate shaft of a medical device, may enter the lumen of the first connection tube 26 (the retrieval device 38 is depicted within the lumen of the first connection tube 26 via dashed lines).

FIG. 5A illustrates the mechanism by which the retrieval device 38 is advanced (or retracted) into and out of the working channel of the elongate shaft 20 (as described above) via manipulation of the first thumbwheel 56. As described above, the clockwise rotation (depicted by arrow 85) of the first thumbwheel 56 will result in the counterclockwise rotation (depicted by arrow 86) of the first drive wheel 58. The counterclockwise rotation of the first drive wheel 58 will translate the retrieval device 38 in a distal direction (e.g., it will drive/push the retrieval device 38 into the lumen of the first connection tube 26). Additionally, it can be appreciated that the counterclockwise rotation of the first thumbwheel 56 reverses the rotation of the first drive wheel 58 and thereby retracts the retrieval device 38 proximally.

It can be appreciated that the ability of the first drive wheel 58 to translate the retrieval device 38 relative to the first connection tube 26 and the working channel of the elongate shaft 20 is created via a compressive force imparted onto the retrieval device 38 as it is sandwiched between the first drive wheel 58 and the first roller wheel 60. It can be further appreciated that the first drive wheel 58 and the first roller wheel 60 must be spaced apart from one another to permit the first drive wheel 58 to sufficiently advance the retrieval device 38 within the first connection tube 26 (and the working channel of the elongate shaft 20) without slipping while also making the tactile feedback of the first thumbwheel 56 comfortable for the user. In some examples, the first drive wheel 58 and/or the first roller wheel 60 may be attached to a spring such that the spacing between first drive wheel 58 and/or the first roller wheel 60 is adjustable for elongate shafts of medical devices having varying outer diameters.

Figure 5B:
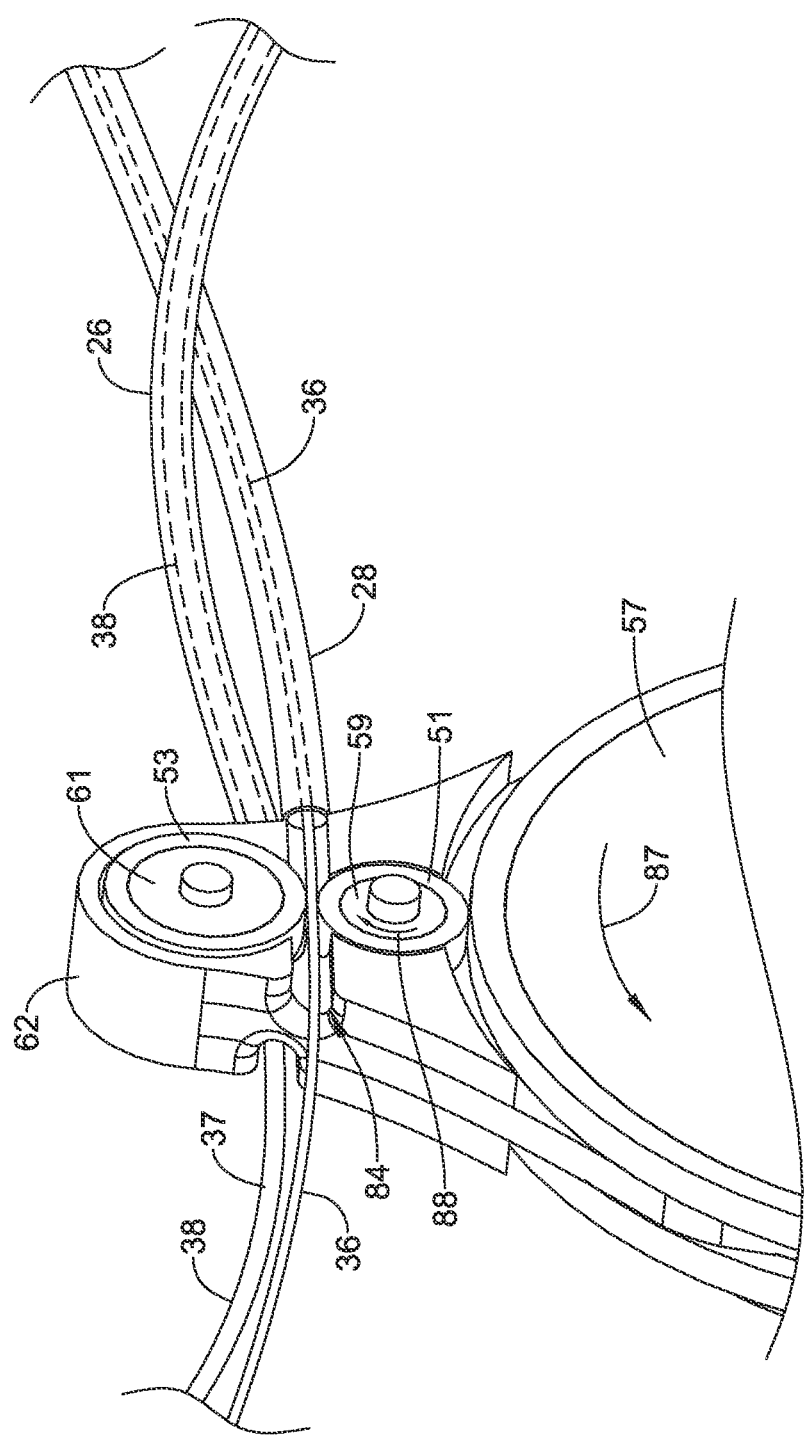
FIG. 5B is another detailed view of the shaft advancement mechanism of the medical device shown in FIG. 1.

FIG. 5B illustrates FIG. 5A rotated to show the laser fiber 36 extending through an opening 84 formed in the inner housing 62. Further, FIG. 5B illustrates that the laser fiber 36 may be sandwiched (i.e., pressed) between the second drive wheel 59 and the second roller wheel 61 (e.g., between the band of material 51 of second drive wheel 59 and the band of material 53 of the first roller wheel 61).

FIG. 5B further illustrates the proximal end of the second connection tube 28 may be fixedly attached to the housing, such as the inner housing 62. For example, the proximal end of the second connection tube 28 may be adhesively attached to the inner housing 62. Other attachment methods are contemplated to fixedly attach the proximal end of the second connection tube 28 to the housing (e.g., the inner housing 62). For example, the proximal end of the second connection tube 28 may be flared while the housing 62 may include a projection designed to engage and mate with the flared portion of the second connection tube 28. In other examples, the proximal end of the second connection tube 28 may be expanded over a barb fitting of the housing 62. Additionally, FIG. 5B illustrates that after passing between the second drive wheel 59 and the second roller wheel 61, the laser fiber 36, or other elongate shaft of a medical device, may enter the lumen of the second connection tube 28 (the laser fiber 36 is depicted within the lumen of the second connection tube 28 via dashed lines).

FIG. 5B illustrates the mechanism by which the laser fiber 36 is advanced (or retracted) into and out of the working channel of the elongate shaft 20 (as described above) via manipulation of the second thumbwheel 57. As described above, the counterclockwise rotation (depicted by arrow 87) of the second thumbwheel 57 will result in the clockwise rotation (depicted by arrow 88) of the second drive wheel 59. The clockwise rotation of the second drive wheel 59 will translate the laser fiber 36 in a distal direction (e.g., it will drive/push the laser fiber 36 into the lumen of the second connection tube 28). Additionally, it can be appreciated that the clockwise rotation of the second thumbwheel 57 reverses the rotation of the second drive wheel 59 and thereby retracts the laser fiber 36 proximally.

It can be appreciated that the ability of the second drive wheel 59 to translate the laser fiber 36 relative to the second connection tube 28 and the working channel of the elongate shaft 20 is created via a compressive force imparted onto the laser fiber 36 as it is sandwiched between the second drive wheel 59 and the second roller wheel 61. It can be further appreciated that the second drive wheel 59 and the second roller wheel 61 must be spaced apart from one another to permit the second drive wheel 59 to sufficient advance the laser fiber 36 within the second connection tube 28 (and the working channel of the elongate shaft 20) without slipping while also making the tactile feedback of the second thumbwheel 57 comfortable for the physician. In some examples, the second drive wheel 59 and/or the second roller wheel 61 may be attached to a spring such that the spacing between second drive wheel 59 and/or the second roller wheel 31 is adjustable for elongate shafts of medical devices having varying outer diameters.

FIGS. 6-10 illustrate another example medical device 100. The medical device 100 is may be similar in form and function to the medical device 10 described above. For example, the medical device 100 may include a handle 112 having a distal end region 114, a proximal end region 116 and a medial region 118. The handle 112 may further include an elongate shaft 120 which extends distally away from the distal end region 114 of the handle 112. The elongate shaft 120 may be similar in form and function to the elongate shaft 20 described above.

Figure 6:
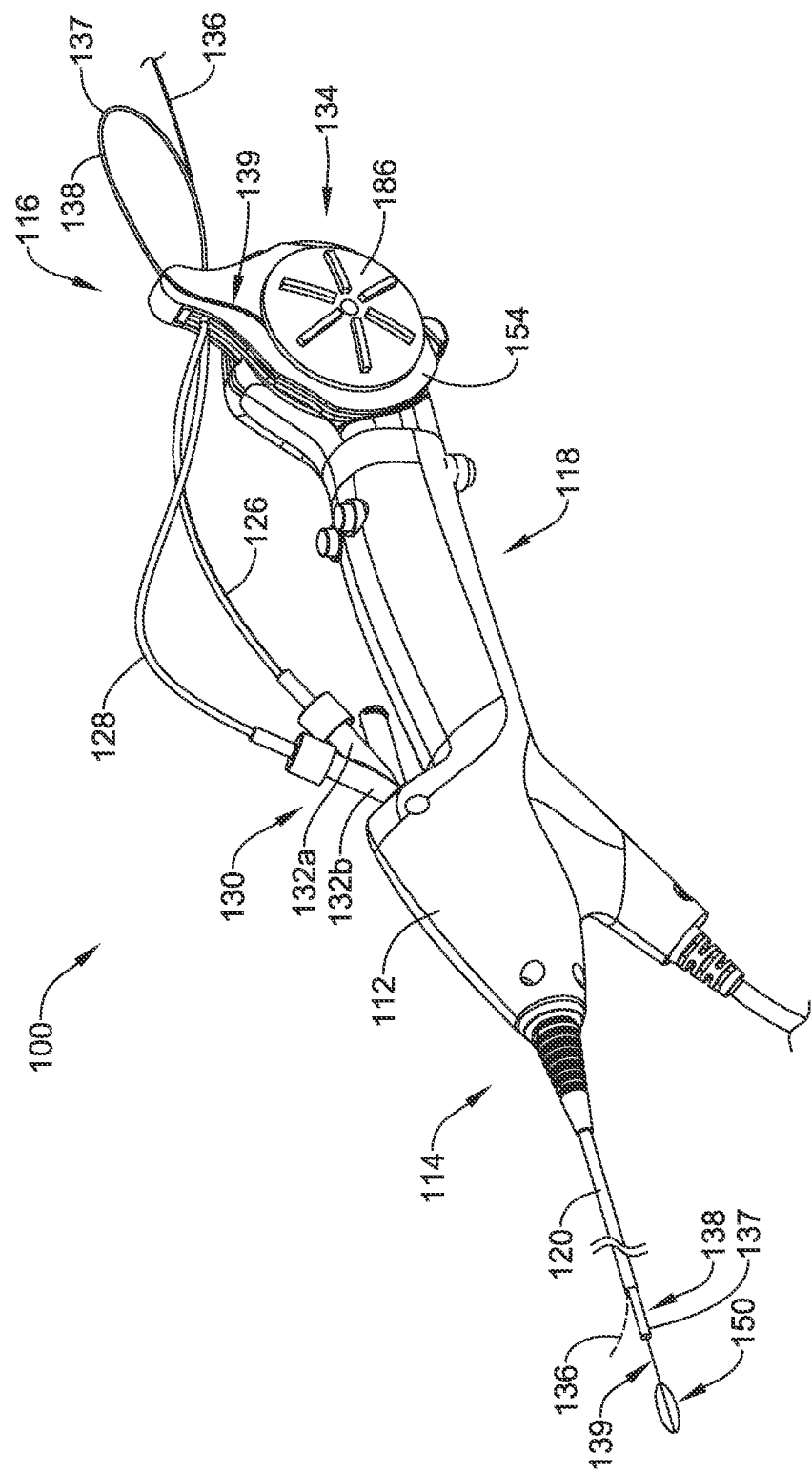
FIG. 6 is a perspective view of another example medical device.

Further, the handle 112 may include an access port 130 (including a first hub 132a and second hub 132b), a first connection tube 126, a second connection tube 128, a retrieval device 138 extending within the first connection tube 126, a laser fiber 136 extending within the second connection tube 128, which are all similar in form and function to the access port 30 (including the first hub 32a and the second hub 32b), the first connection tube 26, the second connection tube 28, the laser fiber 36, and the retrieval device 38, described above with respect to the medical device 10. FIG. 6 further illustrates the retrieval device 138 extending through the lumen of the elongate shaft 120 and out the distal end of the elongate shaft 120 while the distal end of the laser fiber 136 is shown in dashed lines simply for illustrative purposes. Therefore, it can be appreciated that during a medical procedure, only one or the other of the laser fiber 136 or the retrieval device 138 (including the retrieval wire 139 positioned within the lumen of the tubular shaft 137 of the retrieval device 138) may occupy the working channel of the elongate shaft 120 while the other of the laser fiber 136 and the retrieval device 138 may be positioned proximal of the access port 130 within either of the first connection tube 126 or the second connection tube 128. In other instances, the laser fiber 136 may occupy a first working lumen of the elongate shaft 120 while the retrieval device 138, including the tubular shaft 137 of the retrieval device 138 and retrieval wire 139 extending therethrough, occupies the second working lumen of the elongate shaft 120. It can be appreciated that, in some examples, each of the first connection tube 126 and the second connection tube 128 may be transparent or translucent, thereby permitting a clinician to visualize the distal end of the laser fiber 136 or the distal end of the retrieval device 138 located therein when withdrawn from the working channel of the elongate shaft 120 to permit the other device to occupy the working channel of the elongate shaft 120. It may be desirable for a clinician to be able to visually confirm that the distal end of the retrieval device 138 or the distal end of the laser fiber 136 is located in either the first connection tube 126 or the second connection tube 128, respectively, when the other of the retrieval device 138 and the laser fiber 136 is advanced distally into the working channel of the elongate shaft 120. Additionally, FIG. 6 shows the retrieval wire 139, including the retrieval basket 150, extending through the lumen of the tubular shaft 137 of the retrieval device 138 and distally beyond the tubular shaft 137 of the retrieval device 138.

Further, the handle 112 may include a shaft advancement device 134. The shaft advancement device 134 is similar, but not identical, to the shaft advancement device 34 described above. For example, the shaft advancement device 134 may be removably attached (or fixedly attached) to the handle 112 as described above with respect to the shaft advancement device 34. Further, while not visible in FIG. 6, the shaft advancement device 134 may include a first thumbwheel (not visible in FIG. 6) which may be utilized to advance/retract the retrieval device 138 and a second thumbwheel (not visible in FIG. 6) utilized to advance/retract the laser fiber 136.

However, as will be described in detail below, the shaft advancement device 134 further includes a rotatable cap 186, or other actuation mechanism, attached to the housing, such as the outer housing 154 (the outer housing 154 may be similar in form and function to the outer housing 54 described above), whereby the cap 186 may be utilized to longitudinally advance/retract the retrieval wire 139 within and relative to the tubular shaft 137 of the retrieval device 138.

Figure 7:
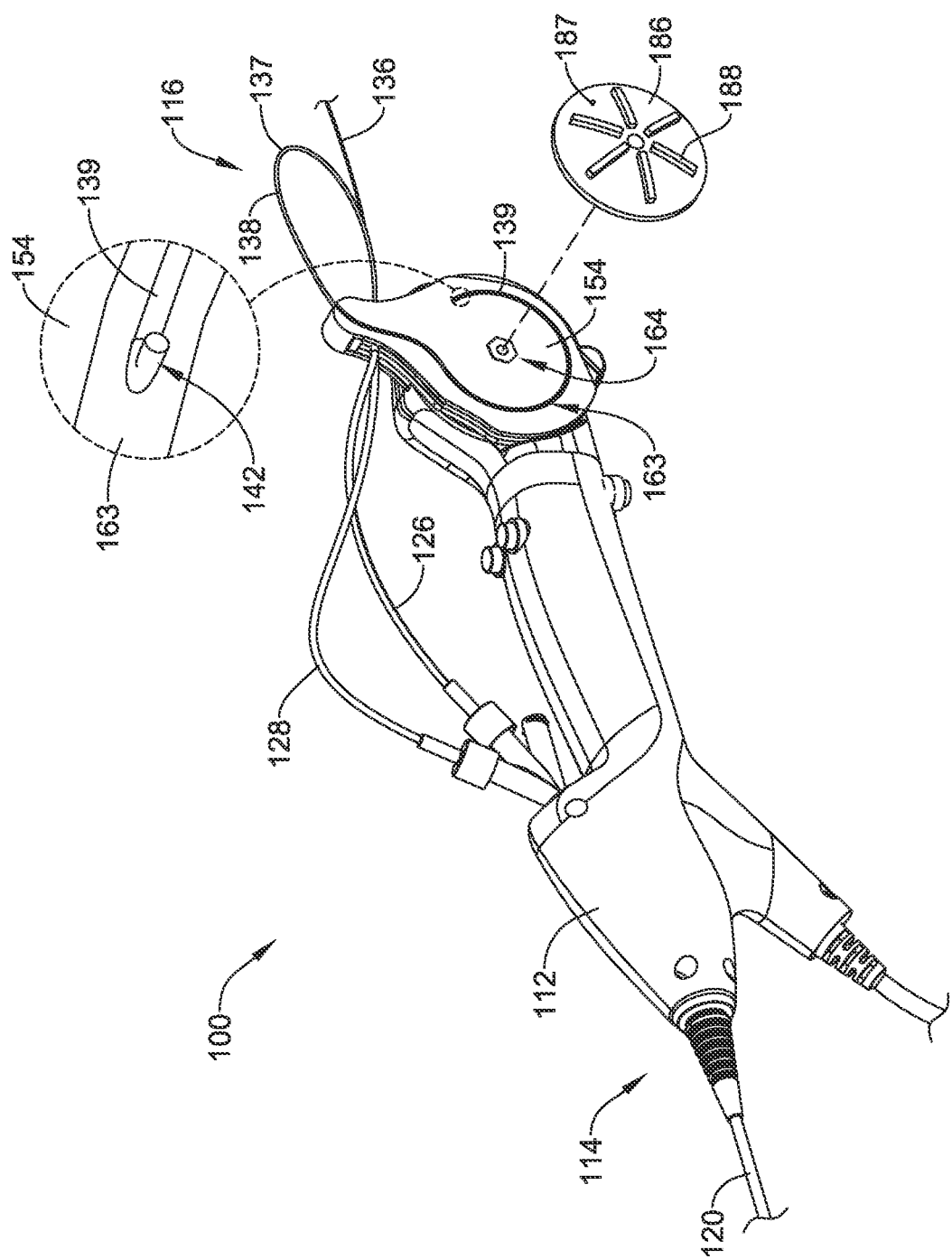
FIG. 7 is another perspective view of the example medical device shown in FIG. 6.

FIG. 7 illustrates the medical device 100 whereby the rotatable cap 186 has been removed from the outer housing 154 of the shaft advancement device 134 to reveal the lateral face (e.g., outer-facing surface) of the outer housing 154. It can be appreciated that the rotatable cap 186 may be coupled to the outer housing 154 via a connection (e.g., a screw/bolt connection) which permits the rotatable cap 186 to rotate around the same axis as the axle 164 (the axle 164 may be similar in form and function to the axle 64 described above). Additionally, FIG. 7 illustrates that the rotatable cap 186 may include one or more projections 188 spaced around the outer surface of the rotatable cap 186. It can be appreciated that the projections 188 may improve a physician's grip when rotating the rotatable cap 186.

Further, FIG. 7 illustrates that the lateral face of the outer housing 154 may include a channel 163. As shown in FIG. 7, the channel 163 may curve and generally follow the perimeter of the outer housing 154 at a radial distance from the axle 164. Additionally, as will be described in greater detail below, the channel 163 may be designed to permit a portion of the tubular shaft 137 of the retrieval device 138 and a portion of the retrieval wire 139 to be positioned therein. Specifically, the proximal end of the tubular shaft 137 of the retrieval device 138 may be fixedly attached within the channel 163 (near the upper portion of the outer housing 154) while the retrieval wire 139 may be free to translate within (e.g., along) the channel 163.

Further, it can be appreciated that when fully assembled, the rotatable cap 186 may be free to rotate around (about) the axle 164 and along the surface of the outer housing 154. Additionally, the detailed view of FIG. 7 illustrates that the proximal end 142 of the retrieval wire 139 may project away from the channel 163 and away from the lateral surface of the outer housing 154 and engage a recess 187 located on the back side of the rotatable cap 186. In other words, the proximal end 142 of the retrieval wire 139 may be fixedly attached (via adhesive, for example) to the back side of the rotatable cap 186. Other attachment techniques are contemplated for fixedly attaching the proximal end 142 of the retrieval wire 139 to the rotatable cap 186. For example, the proximal end 142 of the retrieval wire 139 may be attached to the rotatable cap 186 via adhesive.

Figure 8:
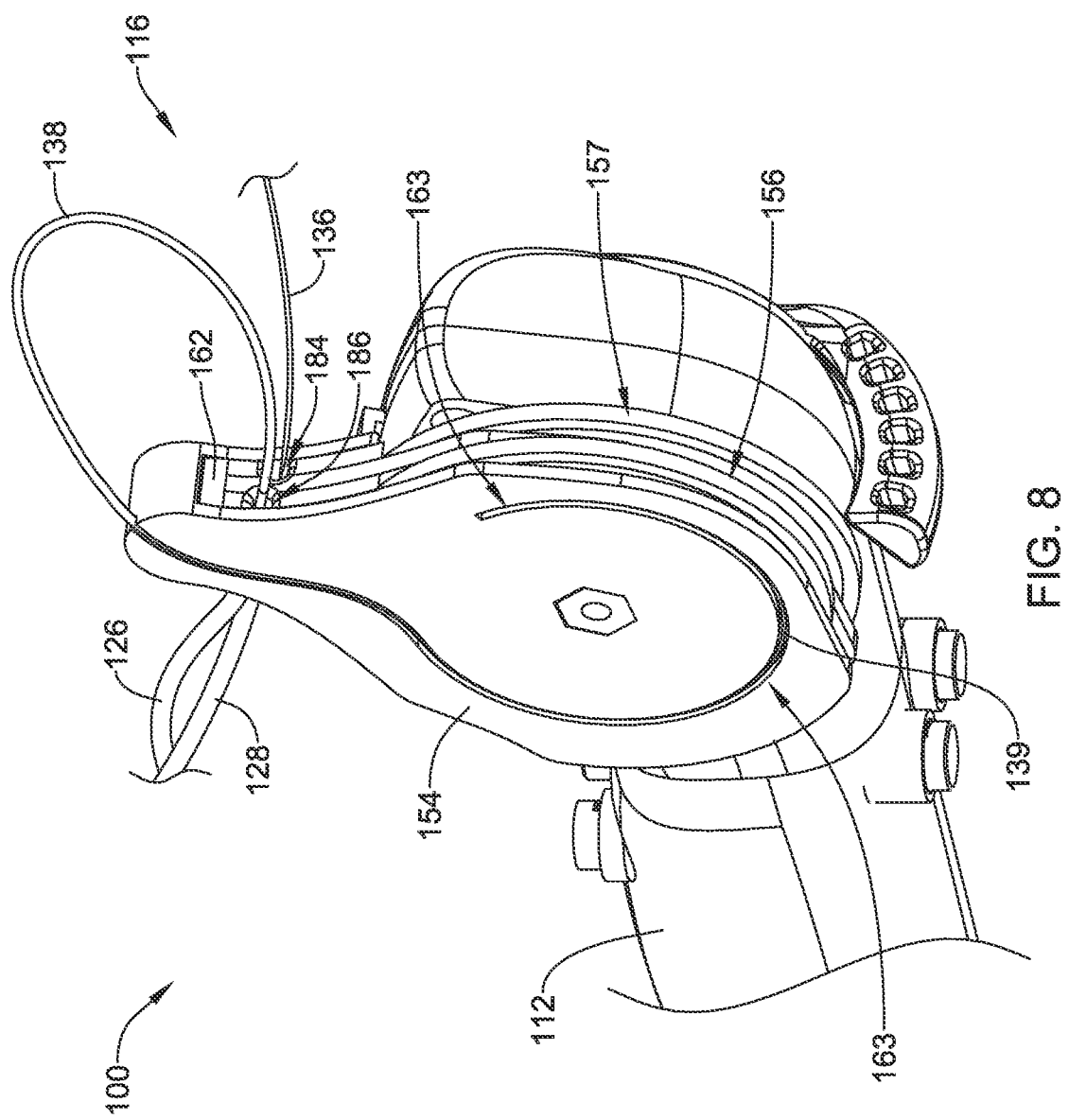
FIG. 8 is a detailed view of the shaft advancement mechanism of the medical device shown in FIG. 7.

FIG. 8 illustrates a perspective view of the proximal end region 116 of the medical device 100 described above. As discussed above, FIG. 8 illustrates that first thumbwheel 156 and the second thumbwheel 157 may be rotatably coupled to the housing, such as the inner housing 162. Additionally, FIG. 8 illustrates the laser fiber 136 extending through an aperture 184 and into the second connection tube 128 and the retrieval sheath 138 extending through an aperture 186 and into the first connection tube 126. While not all the components of the shaft advancement device 134 are shown, it can be appreciated that the operation of using the first thumbwheel 156 and the second thumbwheel 157 to drive (e.g., longitudinally translate) the retrieval sheath 138 and the laser fiber 136 into the first connection tube 126 and the second connection tube 128, respectively, may be similar in form and function as the operation of the first thumbwheel 56 and the second thumbwheel 57 described above. In other words, while not shown in FIG. 7, the shaft advancement device 134 may include the arrangement and function of the drive wheels 58/59 and the roller wheels 60/61 described above. Additionally, FIG. 8 illustrates the retrieval wire 139 positioned within the channel 163 of the outer housing 154.

Figure 9:
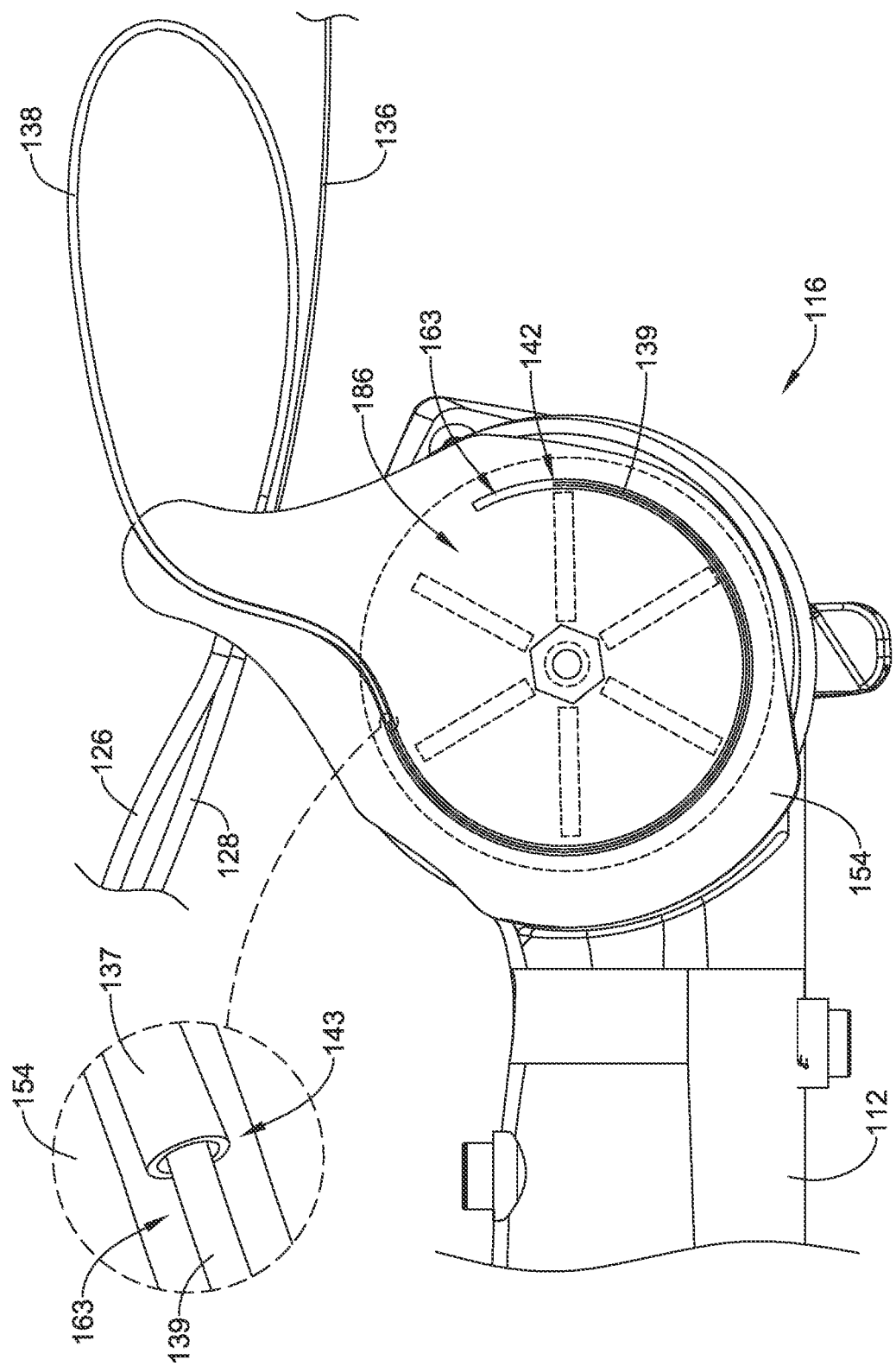
FIGS. 9-10 illustrate example steps in advancing a wire within a portion of the medical device shown in FIGS. 6-8.
Figure 10:
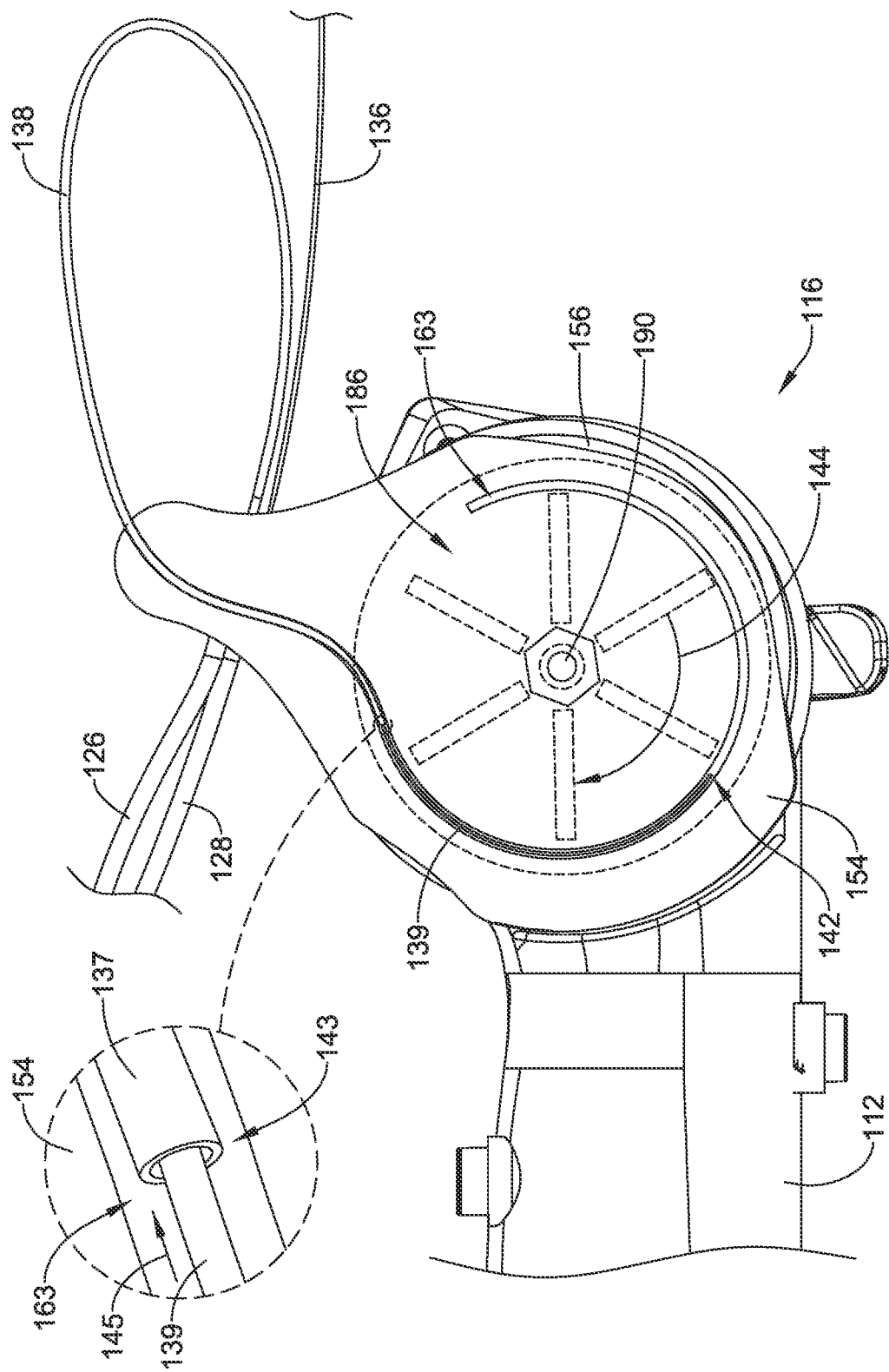

FIGS. 9-10 illustrate the rotation of the rotatable cap 186 relative to the outer housing 154 to advance (and retract) the retrieval wire 139 within the lumen of the tubular shaft 137 of the retrieval device 138. As described above, the detailed view of FIG. 9 illustrates that the proximal end 143 of the tubular shaft 137 of the retrieval device 138 may be fixedly attached to the outer housing 154, such as fixedly attached within the channel 163 of the outer housing 154. For example, the proximal end 143 of the tubular shaft 137 of the retrieval device 138 may be adhesively glued within the channel 163. Therefore, the proximal end 143 of the tubular shaft 137 of the retrieval device 138 may not move relative to the outer housing 154. Further, the detailed view illustrates the retrieval wire 139 extending into the lumen of the tubular shaft 137 of the retrieval device 138, as described above.

FIG. 9 further illustrates the retrieval wire 139 extending along the curvature of the channel 163. It can be further appreciated that FIG. 9 shows the rotatable cap 186 attached to the outer housing 154 of the handle 112 (for simplicity, the rotatable cap 186 is shown as a dotted outline). As described above, in this configuration, the proximal end 142 of the retrieval wire 139 may be understood as extending out of the page whereby it is fixedly attached to the back side of the rotatable cap 186.

FIG. 10 illustrates the rotation of the rotatable cap 186 to longitudinally translate the retrieval wire 139 relative to and within the lumen of the tubular shaft 137 of the retrieval device 138. It can be appreciated that translating the retrieval wire 139 within the lumen of the tubular shaft 137 of the retrieval device 138 may expand and contract a retrieval basket 150 (shown in FIG. 6) attached to the distal end of the retrieval wire 139. Therefore, it can be further appreciated that prior to the physician rotating the cap 186 to deploy the retrieval basket 150, for example, the physician may manipulate the first thumbwheel 156 to advance or retract the retrieval device 138, including the tubular shaft 137 and the retrieval wire 139 of the retrieval device 138, relative to a target site. In other words, as described above, manipulation of the first thumbwheel 156 may move the retrieval device 138, including the tubular shaft 137 and the retrieval wire 139 of the retrieval device 138 simultaneously through the working channel of the elongate shaft 120 of the medical device 100 (e.g., the retrieval wire 139 travels with the tubular shaft 137 of the retrieval device 138 when the retrieval device 138 is manipulated by the first thumbwheel 156). However, to actuate (e.g., deploy or contract) the retrieval basket 150 (attached to the distal end of the retrieval wire 139), the physician may rotate the rotatable cap 186 (using the same hand) which translates the retrieval wire 139 within the channel 163 and the lumen of the tubular shaft 137 of the retrieval device 138 (the rotation of the rotatable cap 186 is depicted by the arrow 144). In other words, because the proximal end 143 of the tubular shaft 137 of the retrieval device 138 is fixedly attach to the outer housing 154, rotation of the rotatable cap 186 only translates the retrieval wire 139 relative to both the outer housing 154 (within the channel 163) and the tubular shaft 137 of the retrieval device 138. The translation of the retrieval wire 139 relative to the outer housing 154 and the tubular shaft 137 of the retrieval device 138 is illustrated by the arrow 145 in the detailed view of FIG. 10. Further, it is noted that FIG. 10 illustrates the rotational displacement of the proximal end 142 of the retrieval wire 139 after the rotatable cap 186 has been rotated.

FIG. 11-15 illustrate another example medical device 200. The medical device 200 may be similar in form and function to the medical devices 10/100 described above. For example, the medical device 200 may include a handle 212 having a distal end region 214 and a proximal end region 216. The handle 212 may further include an elongate shaft 220 which extends distally away from the distal end region 214 of the handle 212. The elongate shaft 220 may be similar in form and function to the elongate shaft 20/120 described above.

Figure 11:
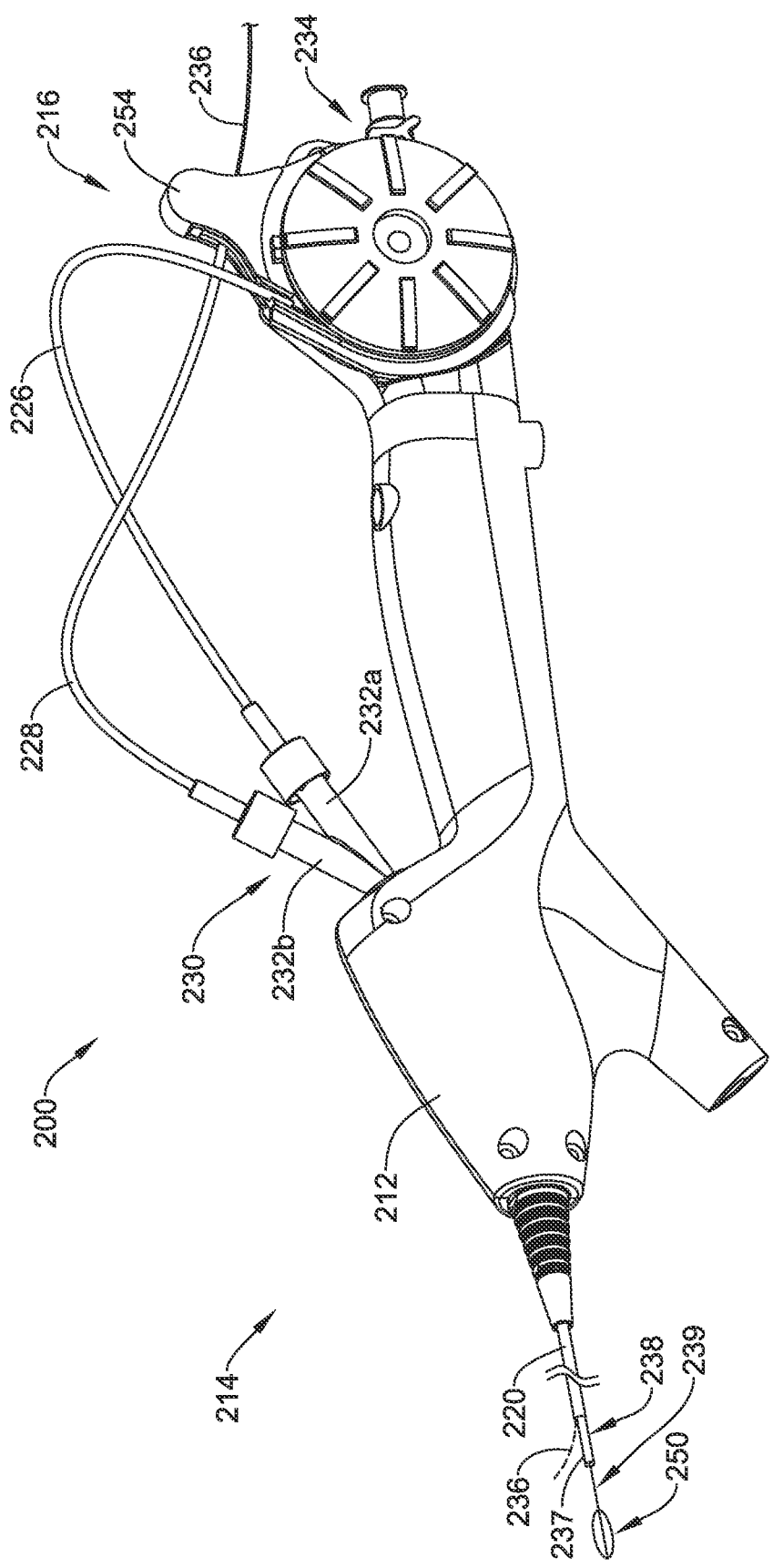
FIG. 11 is a perspective view of another example medical device.

Further, the handle 212 may include an access port 230 (including a first hub 232a and second hub 232b), a first connection tube 226, a second connection tube 228, a retrieval device 238, or other elongate medical device, extending within the first connection tube 226 and into a working channel of the elongate shaft 220 of the medical device 200, laser fiber 236 extending within the second connection tube 228 and into the working channel or another working channel of the elongate shaft 220 of the medical device 200, which may all be similar in form and function to the access port 30/130 (including the first hub 32a/132a and the second hub 32b/132b), the first connection tube 26/126, the second connection tube 28/128, the laser fiber 36/136, and the retrieval sheath 38/138, described above with respect to the medical devices 10/100. FIG. 11 further illustrates the retrieval device 238 extending through the lumen of the elongate shaft 220 and distally out from the distal end of the elongate shaft 220, while the distal end of the laser fiber 236 is shown in dashed lines simply for illustrative purposes. Therefore, it can be appreciated that during a medical procedure, only one or the other of the laser fiber 236 or the retrieval device 238 (including the retrieval wire 239 positioned within the lumen of the tubular shaft 237 of the retrieval device 238) may occupy the working channel of the elongate shaft 220 while the other of the laser fiber 236 and the retrieval device 238 may be positioned proximal of the access port 230 within either of the first connection tube 226 or the second connection tube 228. In other instances, the laser fiber 236 may occupy a first working lumen of the elongate shaft 220 while the retrieval device 238, including the tubular shaft 237 of the retrieval device 238 and retrieval wire 239 extending therethrough, occupies the second working lumen of the elongate shaft 220. It can be appreciated that, in some examples, each of the first connection tube 226 and the second connection tube 228 may be transparent or translucent, thereby permitting a clinician to visualize the distal end of the laser fiber 236 or the distal end of the retrieval device 238 located therein when withdrawn from the working channel of the elongate shaft 220 to permit the other device to occupy the working channel of the elongate shaft 220. It may be desirable for a clinician to be able to visually confirm that the distal end of the retrieval device 238 or the distal end of the laser fiber 236 is located in either the first connection tube 226 or the second connection tube 228, respectively, when the other of the retrieval device 238 and the laser fiber 236 is advanced distally into the working channel of the elongate shaft 220. Additionally, FIG. 11 shows the retrieval wire 239, including the retrieval basket 250, extending through the lumen of the tubular shaft 237 of the retrieval device 238 and distally beyond the tubular shaft 237 of the retrieval device 238.

Figure 12:
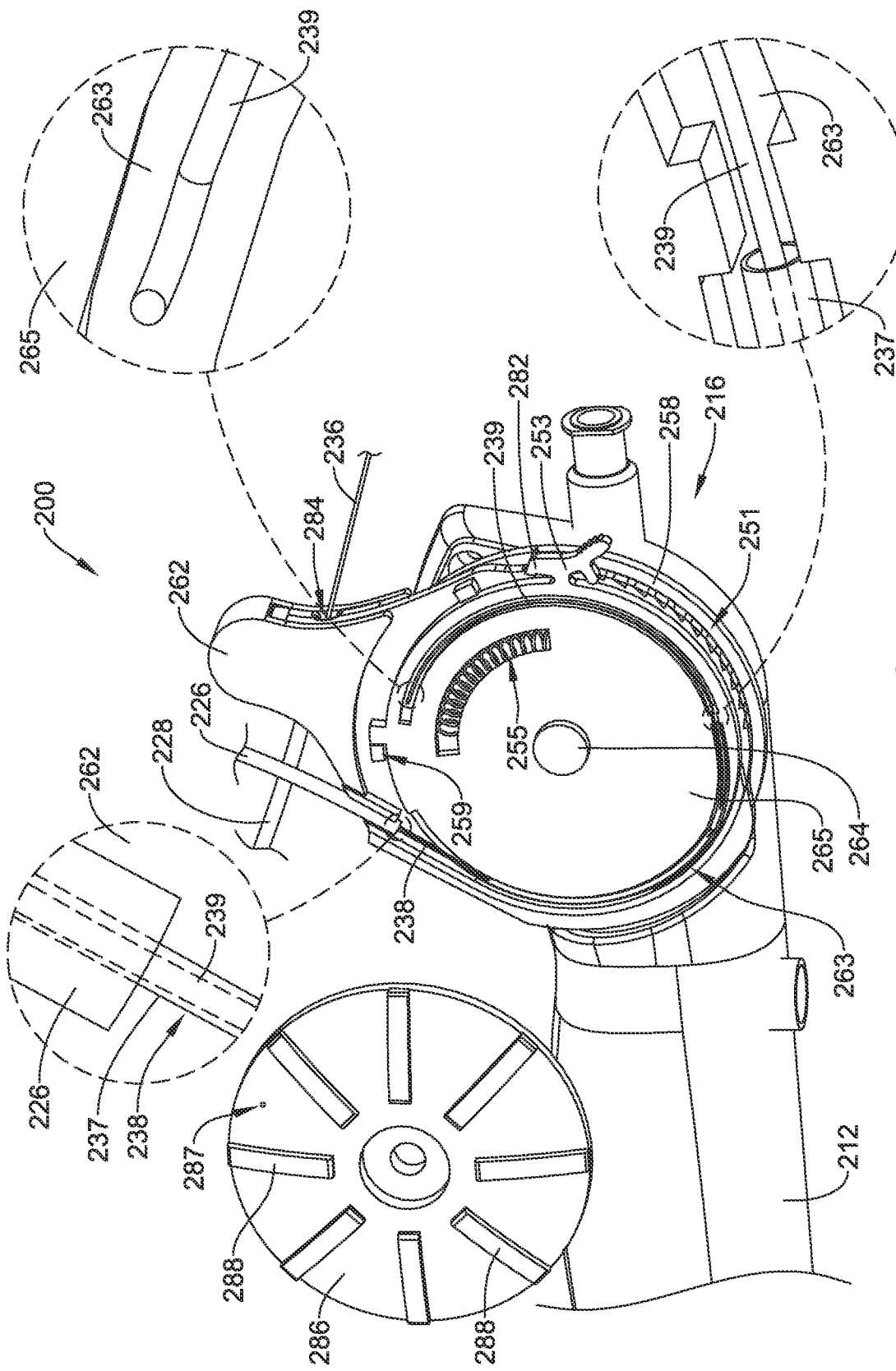
FIG. 12 is a detailed view of the shaft advancement mechanism of the medical device shown in FIG. 11.

Additionally, FIG. 12 illustrates that the handle 212 may include a shaft advancement device 234. The shaft advancement device 234 may be similar to the shaft advancement device 34 described above. For example, the shaft advancement device 234 may be removably (or fixedly) attached to the handle 212 as described above with respect to the shaft advancement device 34 described with respect to the medical device 10.

FIG. 12 illustrates a detailed view of the proximal end region 216 of the handle 212. Similar to that described above, FIG. 12 illustrates that the rotatable cap 286 may include one or more projections 288 which are spaced around the outer surface of the rotatable cap 286. It can be appreciated that the projections 288 may improve a physician's grip when rotating the rotatable cap 286. For clarity, FIG. 12 illustrates that the rotatable cap 286 has been spaced away from the handle 212.

Further, FIG. 12 illustrates that the shaft advancement device 234 includes an inner housing 262 which may be similar in form and function to the inner housings 62/162 described above. However, unlike the inner housings 62/162 described above, the inner housing 262 may include only a single thumbwheel 258, or it may include first and second thumbwheels if desired. The form and function of the thumbwheel 258 may be similar to the thumbwheel 58/158 described above. For example, the thumbwheel 258 may be coupled to the laser fiber 236 via a drive wheel (not visible in FIG. 12). Additionally, the laser fiber 236 may extend through an aperture 284 located in the inner housing 262, whereby the laser fiber 236 is sandwiched between a drive wheel and a roller wheel (neither the drive wheel nor roller wheel are visible in FIG. 12). Accordingly, as described above, the thumbwheel 258 may be utilized to advance/retract the laser fiber 236 into the second connection tube 228, and thus through the working channel of the elongate shaft 220 of the medical device 200, in a manner similar to that described above with respect to the medical devices 10/100.

However, the shaft advancement device 234 may differ from the shaft advancement devices 34/134 described above in that the advancement/retraction of the retrieval device 238 and/or the retrieval wire 239 of the retrieval device 238 may be accomplished via a cooperative relationship between a rotation disk 265 and the rotatable cap 286. It is noted that, in some examples, the rotation disk 265 may be positioned in the same relative location on the shaft advancement device 234 as the first thumbwheel 56/156 is positioned in the medical devices 10/100 described above. In other words, the rotation disk 265, which may also be considered a thumbwheel of the shaft advancement device 234, having been considered to have taken the place of the first thumbwheel 56/156 in the medical devices 10/100 described above.

FIG. 12 illustrates that the rotation disk 265 may be coupled to the inner housing 262 via the extension of an axle 264 of the inner housing 262 through an aperture of the rotation disk 265. FIG. 12 illustrates that the axle 264 of the inner housing 262 may be generally located in a central region of the inner housing 262. It can be further appreciated that the rotation disk 265 may be rotated around the axle 264 via manipulation of a thumb lever 253. For example, it can be appreciated that a physician may use a thumb to manipulate the lever 253 and rotate the rotation disk 265 about the axle 264.

Additionally, FIG. 12 illustrates that the shaft advancement device 234 may include a locking mechanism to lock the position of the retrieval device relative to the elongate shaft of the medical device. 220 at one of a plurality of positions. For example, the inner housing 262 may include a plurality of teeth 251 positioned along an outer perimeter of the inner housing 262 and adjacent to the lever 253. Additionally, it can be appreciated that the lever 253 may include a projection 282 which engages the teeth 251 and locks the rotation disk 265 in a fixed position when the projection 282 is seated between two adjacent teeth 251. When in a locked position, the rotation disk 265 may be prevented from rotating in a clockwise and/or a counter-clockwise direction. For example, in the example shown in FIG. 12, the thumb lever 253 may be utilized to rotate the rotation disk 265 about the axle 264. For example, a force exerted on the thumb lever 253 by a user's thumb (or other finger) may flex the thumb lever 253 to disengage the projection 282 from between adjacent teeth 251, thereby allowing the rotation disk 265 to be rotated. However, when the rotation disk 265 stops rotating and the force is removed, the projection 282 may revert back toward the axle 264 and engage a flat backside portion of a given tooth 251, thereby preventing the rotation disk 265 from freely rotating in a clockwise direction. It can be appreciated that to rotate the rotation disk 265 in a clockwise direction, a physician may press the thumb lever 253, which flexes the projection 282 away from the axle 264 thereby permitting the projection 282 to pass over top of the teeth 251 while the rotation disk 265 rotates clockwise. Thus, the locking mechanism may be used to secure the longitudinal position of the retrieval device 238, and thereby prevent distal movement of the tubular shaft 237 of the retrieval device 238 as the retrieval wire 239 is advanced or retracted via rotation of the rotation cap 286 is rotated, as discussed herein.

In the illustrated embodiment, the flanks of the teeth 251 are formed such that the projection 282 must be actively disengaged by depressing on the thumb lever 253 in order to rotate the rotation disk 265 in a clockwise direction, in order to prevent inadvertent distal advancement of the retrieval device 238. However, due to the acute angle of the flanks of the teeth, counterclockwise rotation may be permitted as the projection 282 slides along the angled flank of the teeth. In another embodiment, the flanks of the teeth 251 may be reversed such that the projection 282 must be actively disengaged by depressing on the thumb lever 253 in order to rotate the rotation disk 265 in a counterclockwise direction, in order to prevent inadvertent proximal withdrawal of the retrieval device 238. However, due to the acute angle of the flanks of the teeth, clockwise rotation may be permitted as the projection 282 slides along the angled flank of the teeth. In another embodiment, the teeth 251 may include a "V" shape, which may function to prevent both the clockwise and counterclockwise rotation of the rotation disk 265 (when the projection is positioned within one of the grooves of the teeth 251.

FIG. 12 further illustrates that the proximal end region of the first connection tube 226 may be fixedly attached to the housing, such as the inner housing 262. For example, the detailed view in the upper left portion of FIG. 12 illustrates that a proximal end of the first connection tube 226 may be fixedly attached to the inner housing 262 via glue or other attachment methods (e.g., press fit, etc.). Further, the detailed view in the upper left portion of FIG. 12 illustrates the retrieval device 238 passing into the lumen of the first connection tube 226. That same detailed view further shows the retrieval wire 239 positioned within the lumen of the tubular shaft 237 of the retrieval device 238 (and by extension, positioned within the lumen of the first connection tube 226). Because the first connection tube 226 is fixedly attached to the inner housing 262, it can be appreciated that the retrieval device 238, including both the tubular shaft 237 of the retrieval device 238 and the retrieval wire 239 may translate relative to and within the first connection tube 226.

FIG. 12 further illustrates the inner housing 262 may include a channel 263 which may curve and generally follow the perimeter of the rotation disk 265 at a radial distance from the axle 264. Further, FIG. 12 illustrates that portions of both the tubular shaft 237 and the retrieval wire 239 of the retrieval device 238 may be positioned within the channel 263. In particular, the detailed view in the lower right corner of FIG. 12 illustrates a location within the channel 263 in which the proximal end region of the tubular shaft 237 of the retrieval device 238 may be fixedly attached to the rotation disk 265. Accordingly, it can be appreciated that rotation of the rotation disk 265 (as described above), may advance or retract the tubular shaft 237 of the retrieval device 238, as well as the retrieval wire 239 therein, relative to and within the first connection tube 226.

Additionally, the detailed view in the upper right corner of FIG. 12 illustrates the retrieval wire 239 positioned within the channel 263 of the rotation disk 265. The retrieval wire 239 may not be fixedly attached to the rotation disk 265. Rather, the detailed view in the upper right corner of FIG. 12 illustrates that the proximal end of the retrieval wire 239 may be bent outwardly such that it may engage and be fixedly attached to a recess 287 positioned along the back side of the rotation cap 286. It is noted that the retrieval wire 239 may be otherwise fixedly attached to the rotation cap 286. Similar to the functionality of the rotation cap 186 described with respect to the medical device 100 above, rotation of the rotation cap 286 may longitudinally translate the retrieval wire 239 within the channel 263 of the rotation disk 265 and through the lumen of the tubular shaft 237 of the retrieval device 238.

However, it can further be appreciated that the rotation cap 286 may be engaged with the rotation disk 265 such that the rotation cap 286 may rotate along with the rotation disk 265 when the rotation disk 265 is rotated (e.g., via the thumb lever 253). In some examples, the backside of the rotation cap 286 may include a projection (not visible in FIG. 12) which extends toward the rotation disk 265 and rests within the channel in which the spring 255 is located. The spring 255 may contact and bias the projection. Therefore the rotation cap 286 may "go along for the ride" with the rotation disk 265 when the rotation disk 265 is rotated such that there is no relative rotation between the rotation cap 286 and the rotation disk 265 when the rotation disk 265 is rotated.

It can be further appreciated that when the rotation disk 265 is rotated (and the rotation cap 286 rotates along with the rotation disk 265) both the tubular shaft 237 of the retrieval device 238 and the retrieval wire 239 will move together within the first connection tube 226 and/or longitudinally through a working channel of the elongate shaft 220. In other words, as the rotation disk 265 is rotated, the rotation disk 265 may translate the tubular shaft 237 of the retrieval device 238 while, simultaneously, the rotation cap 286 (sitting atop of the rotation disk 265) will rotate along with the rotation disk 265 and translate the retrieval wire 239 at the same speed (displacement) as the tubular shaft 237 of the retrieval device 238.

However, it can be appreciated that after the rotation of the rotation disk 265 is stopped and the projection 282 is engaged with the teeth 251 (thereby locking the rotation disk 265 in place relative to the inner housing 262), the rotation cap 286 may be rotated relative to the rotation disk 265 (and, by extension, the inner housing 262). Rotation of the rotation cap 286 relative to the rotation disk 265 may advance (or retract) the retrieval wire 239 relative to the tubular shaft 237 of the retrieval device 238, thus advancing the retrieval basket 250 relative to the tubular shaft 237 of the retrieval device 238.

As discussed above, FIG. 12 illustrates that the handle 212 may include a spring 255 positioned within a recessed channel on the rotation disk 265. As will be described in greater detail below, one end of the spring 255 may be coupled to the back side of the rotation cap 265 (e.g., a similar connection technique may be employed to connect the distal end of the spring 255 to the back side of the rotation cap 286 as was employed to connect the proximal end of the retrieval wire 239 to the back side of the rotation cap 286). Accordingly, the spring 255 may be designed to bias rotation of the rotation cap 286 in a counterclockwise direction after the rotation cap 286 is released after being rotated in clockwise direction. Thus, the spring 255 may be implemented to bias the rotation cap 286, and thus the retrieval wire 239, in a retracted configuration with the retrieval basket 250 collapsed. Rotating the rotation cap 286 in the clockwise direction to overcome the force of the spring 255, causes the retrieval basket 250 to be deployed (e.g., expanded).

Figure 13:
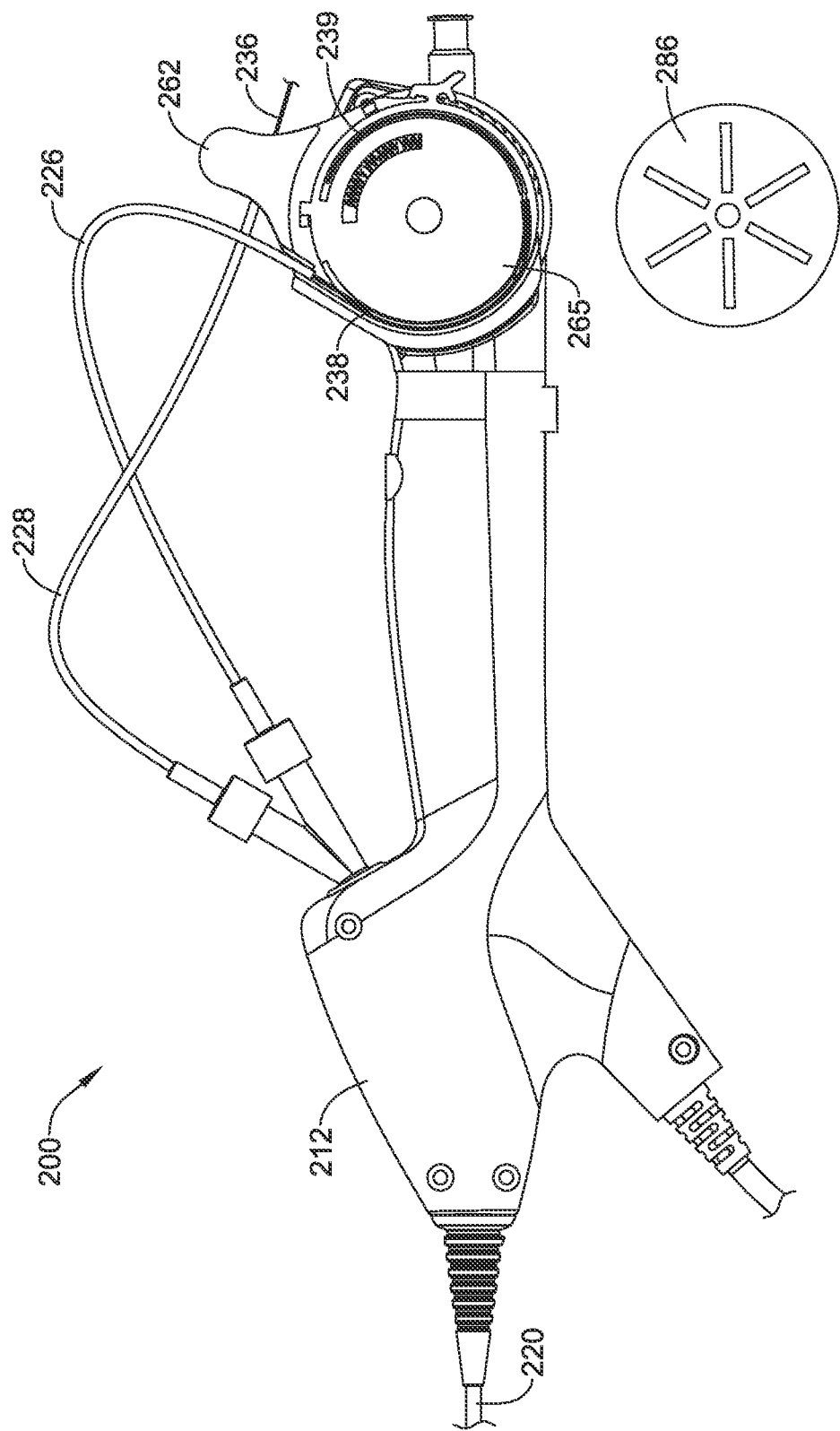
FIGS. 13-15 illustrate example steps in advancing multiple medical device shafts within a portion of the medical device shown in FIGS. 11-12.
Figure 14:
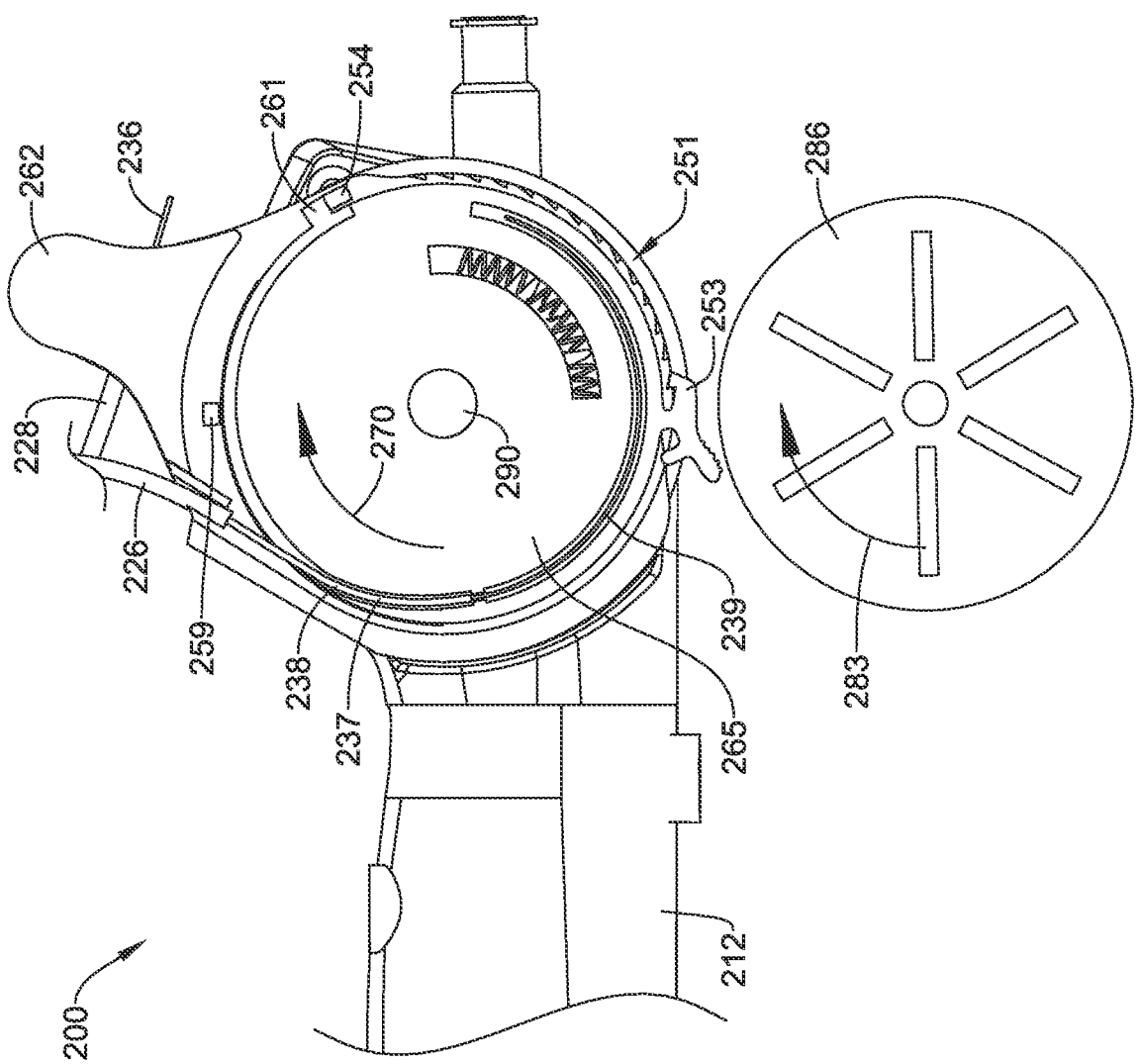
Figure 15:
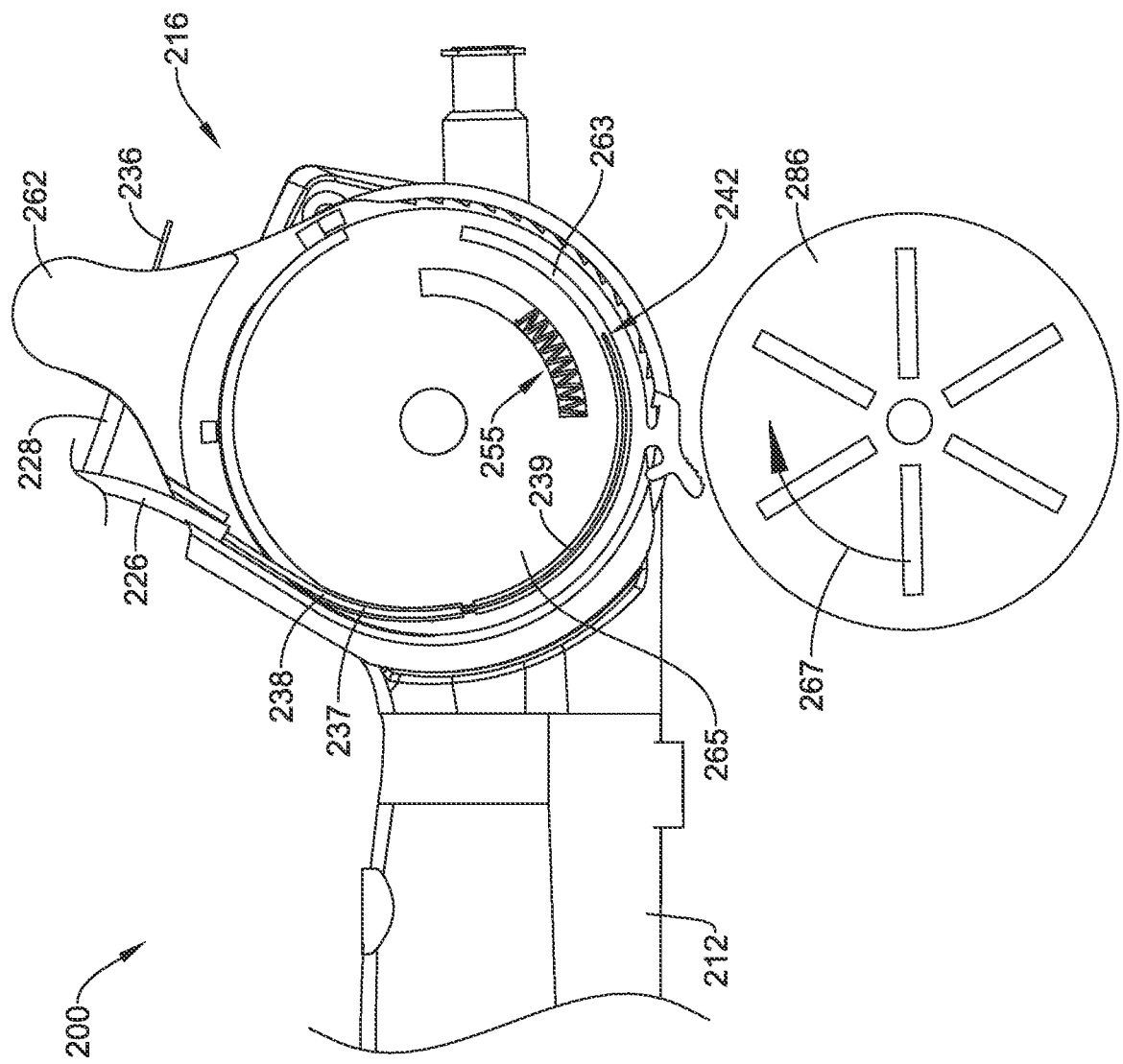

FIGS. 13-15 illustrate the cooperative operation of the rotation disk 265 and the rotation cap 286 to advance/retract, or otherwise manipulate the retrieval device 238. FIG. 13 illustrates a handle configuration in which both the tubular shaft 237 and the retrieval wire 239 of the retrieval device 238 may be located within a working channel of the elongate shaft 220 and positioned just proximal of the distal end of the elongate shaft 220. For clarity, the rotation cap 286 is shown removed from the handle 212. However, it should be understood that for FIGS. 13-15, the rotation cap 286 would be positioned on top of the rotation disk 265 as described above. Additionally, FIG. 13 illustrates that the rotation disk 265 has not been rotated in a clockwise direction and the retrieval wire 239 has not been translated relative to the tubular shaft 237 of the retrieval device 238.

FIG. 14 illustrates the simultaneous rotation of the retrieval disk 265 and the rotation cap 286. As described above, rotation of the rotation disk 265 may be accomplished via manipulation of the thumb lever 253 overtop the plurality of teeth 251. FIG. 14 illustrates that, in some examples, rotation of the rotation disk 265 may be confined between a first stop 259 and a second stop 254. For example, the rotation disk 265 may include a projection 261 which engages the first stop 259 in a fully retracted position. The projection 261 may move into engagement with the second stop 254 as the rotation disk 265 is rotated clockwise to its maximum clockwise position, or fully extended position. This engagement prevents further rotation of the rotation disk 265 in a clockwise direction, and thus prevents further distal advancement of the tubular shaft 237 of the retrieval device 238 out of or otherwise relative to the distal end of the elongate shaft 220. FIG. 14 depicts the rotation of the rotation disk 265 with the arrow 270 and the rotation of the rotation cap (occurring simultaneously with the rotation disk 265) with the arrow 283. As described above, rotation of the rotation disk 265 may translate both the tubular shaft 237 and the retrieval wire 239 of the retrieval device 238 out of the distal end of the elongate shaft 220. FIG. 14 further illustrates that the projection 282 is engaged with the teeth 252, and therefore, preventing the rotation disk 265 from rotating relative to the inner housing 262.

FIG. 15 illustrates the independent rotation of the rotation cap 286 relative to the rotation disk 265 to translate the retrieval wire 239 relative to the tubular shaft 237 of the retrieval device 238 As shown in FIG. 15 the rotation cap 286 may be rotated (rotation of the rotation cap 286 is depicted by the arrow 267) relative to the rotation disk 265 which translates the distal end 242 of the retrieval wire 239 within the channel 263 (it is noted that the position of the distal end 242 of the retrieval wire 239 within the channel 263 in FIG. 14 as compared to its position in FIG. 15 illustrates the translation of the wire 239 within the channel 263). Further, because the rotation disk 265 is held in place in FIG. 15, the tubular shaft 237 of the retrieval device 238 remains stationary while the retrieval wire 239 translates within the lumen of the tubular shaft 237 of the retrieval device 238. It can be appreciated that this translation may deploy (e.g., expand) the basket 250 at the distal end of the retrieval device 238. Additionally, FIG. 15 shows the spring 255 being compressed as the rotation cap 286 is rotated. Accordingly, after the rotation cap 286 is released, expansion of the spring 255 may rotate the rotation cap 286 in a counterclockwise direction, thereby translating the retrieval wire 239 within the channel 263 and collapsing the retrieval basket 250.

Figure 16:
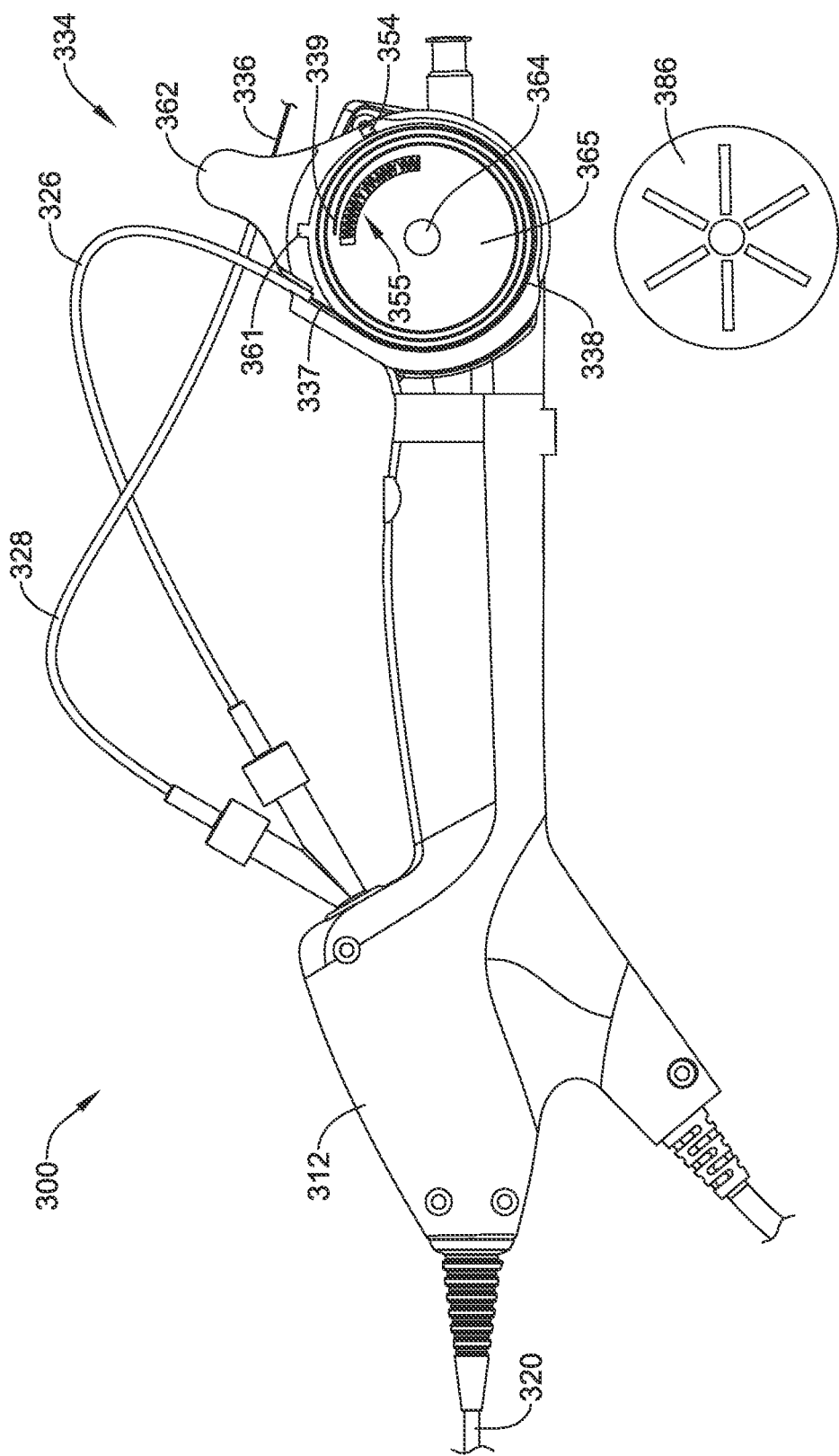
FIG. 16 is a side view of another example medical device.
Figure 17:
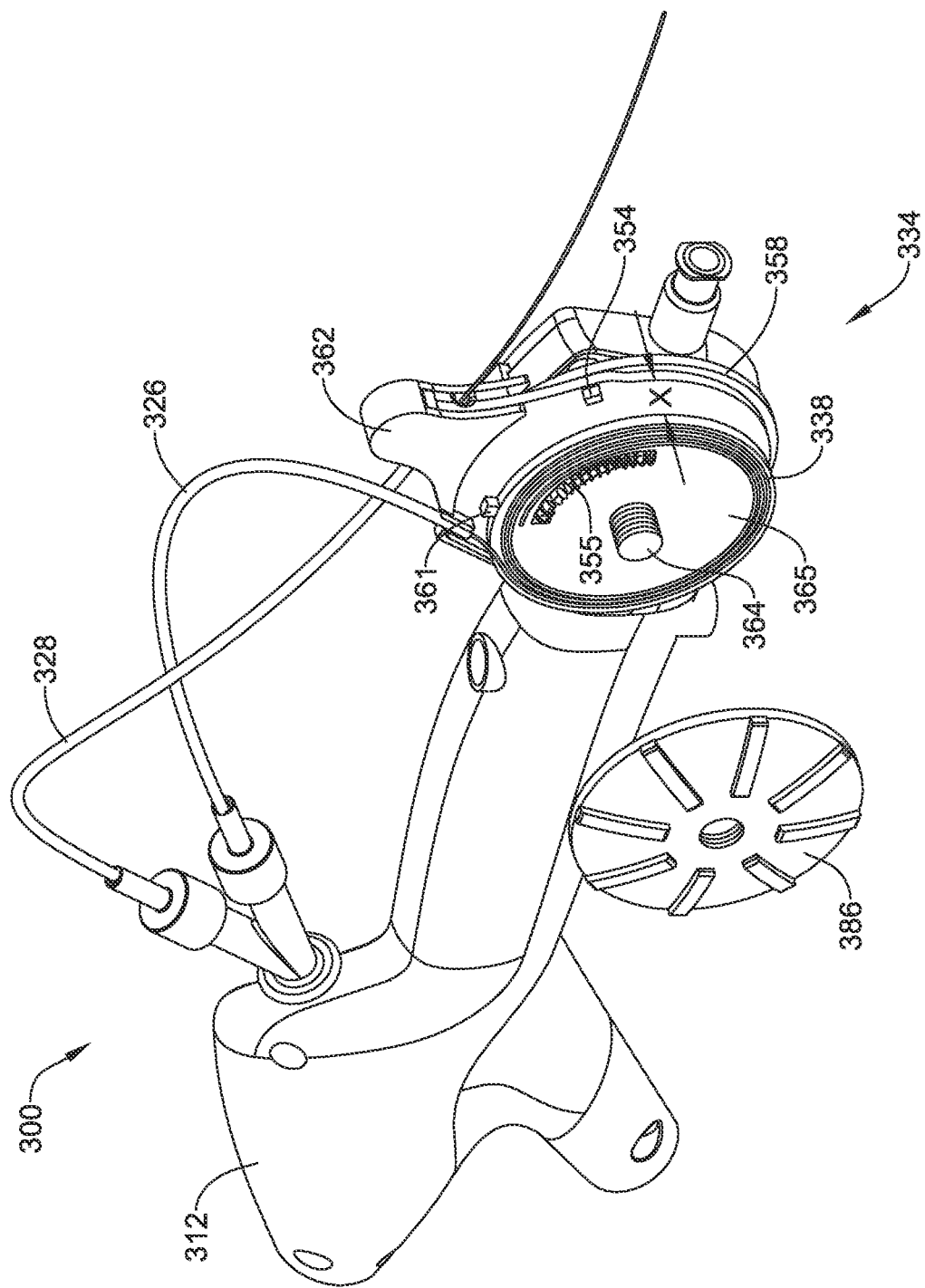
FIG. 17 is a perspective view of the example medical device shown in FIG. 16.

FIG. 16-17 illustrate another example medical device 300. The medical device 300 may be similar in form and function to the medical device 200 described above. For example, the medical device 300 may include a handle 312 having an elongate shaft 320 which extends distally away from the distal end of the handle 312. The elongate shaft 320 may be similar in form and function to the elongate shaft 20 described above.

Further, the handle 312 may include a first connection tube 326, a second connection tube 328, a retrieval device 338, or other elongate medical device, extending within the first connection tube 326 and into a working channel of the elongate shaft 320 of the medical device 300, and a laser fiber 336 extending within the second connection tube 328 and into the working channel or another working channel of the elongate shaft 320 of the medical device 300, which may all be similar in form and function to the first connection tube 26/126/226, the second connection tube 28/128/228, the retrieval device 38/138/238 extending within the first connection tube 26/126/226, and the laser fiber 36/136/236 extending within the second connection tube 28/128/228, described above with respect to the medical devices 10/100/200.

Additionally, FIG. 16 illustrates that the handle 312 may include a shaft advancement device 334. The shaft advancement device 334 may be similar to the shaft advancement device 234 described above. For example, the shaft advancement device 334 may be removably (or fixedly) attached to the handle 312 as described above with respect to the shaft advancement device 234 described with respect to the medical device 200. Further, the operation of the shaft advancement device 334 may be similar in function to the shaft advancement device 234 described above. However, as shown in FIG. 16, the shaft advancement device 334 may not include the teeth 251 or a thumb lever 253 (including a projection 282) as described above with respect to the shaft advancement device 234. Rather, the shaft advancement device 334 may include a configuration in which the elongate tubular shaft 337, and the retrieval wire 339 extending therein, are spooled along the rotation disk 365. Therefore, it can be appreciated that as the rotation disk 365 is rotated (e.g., in a clockwise direction), the retrieval device 338 may be advanced within the first connection tube 326 and/or the working channel extending within the elongate shaft 320.

In some examples, the retrieval device 338 may be spooled around a shelf (e.g., rim, lip, ledge, etc.) located on the rotation disk 365. However, in other examples, the retrieval device 338 may be spooled within a channel extending into the surface of the rotation disk 365, for example.

Additionally, FIG. 16 illustrates that the proximal end of the retrieval wire 339 may extend out of the proximal end of the tubular shaft 337 of the retrieval device 338 and may be coupled to the backside of the rotation cap 386 in a manner similar to that described above with respect to the medical device 200. Similarly, FIG. 16 shows that the shaft advancement device 334 may include a spring 355 resting within a channel located on the rotation disk 365. Similar to that described above with respect to the medical device 200, rotation of the rotation cap 386 may advance the retrieval wire 339 relative to the tubular shaft 337 of the retrieval device 338, thereby deploying (e.g., expanding) an end effector (e.g., retrieval basket) at the distal end of the retrieval device 338. However, as described above, once the rotation cap 386 is released, the spring 355 may expand, thereby rotating the rotation cap 386 in a counterclockwise direction and retracting the retrieval wire 339 proximally relative to the tubular member 337 of the retrieval sheath 338, thereby contracting the retrieval basket. In other words, as described above with respect to the medical device 200, the spring 355 may function to bias a retrieval basket, or other end effector, located on the distal end of the retrieval device 338 toward a closed on contracted configuration.

FIG. 17 is a perspective view of the medical device 300 illustrated in FIG. 16. FIG. 17 illustrates that the shaft advancement device 334 includes an inner housing 362 which may be similar in form and function to the inner housings 62/162/262 described above. The inner housing 362 may include a single thumbwheel 358, or it may include first and second thumbwheels if desired. The form and function of the thumbwheel 358 may be similar to the thumbwheels 58/158/258 described above. For example, the thumbwheel 358 may be coupled to the laser fiber 336 via a drive wheel (not visible in FIG. 17), whereby the laser fiber 336 is sandwiched between a drive wheel and a roller wheel (neither the drive wheel nor roller wheel are visible in FIG. 17). Accordingly, as described above, the thumbwheel 358 may be utilized to advance/retract the laser fiber 336 into the second connection shaft 328 in a manner similar to that described above with respect to the medical devices 10/100/200.

As described above, FIG. 17 illustrates that the retrieval device 338 (including the combination of the tubular shaft 337 of the retrieval device 338 and the retrieval wire 339) may be spooled around the rotation disk 365. Further, it can be appreciated that in an assembled configuration, the tubular shaft 337 of the retrieval device 338 may be positioned between the rotation cap 386 and the rotation disk 365. Further yet, the rotation cap 386 and the rotation disk 365 may be threaded onto a threaded axle 364 such that the rotation cap 386 and the rotation disk 365, together, may be spaced away from the inner housing a distance "X."

In operation, it can be appreciated that a clinician may rotate the rotation disk 365 and the rotation cap 386 in a clockwise direction and thereby advance the retrieval device 338 through the working channel of the elongate shaft 320. As the rotation disk 365 and the rotation cap 386 are threaded onto the threaded axle 364, clockwise rotation of the rotation disk 365 and the rotation cap 386 will move both the rotation disk 365 and the rotation cap 386 toward the lateral face of the inner housing 362. It can be appreciated that the rotation disk 365 and the rotation cap 386 may be rotated clockwise until a projection 361 located on the rotation disk 365 engages a positive stop 354 on the inner housing 362. At this point, the rotation disk 365 is prevented from any further clockwise rotation (which also prevents any further distal translation of the tubular shaft of the retrieval device 338). However, as described above, the rotation cap 386 may still be able to be rotated clockwise (thereby compressing the spring 355) to advance the retrieval wire 339 distally relative to the distal end of the tubular shaft 337 of the retrieval device 338 to thereby open or expand the end effector. Further, releasing the cap 386 allows the spring 355 to expand and rotates the cap 386 in a counterclockwise direction, which retracts the retrieval wire 339 proximally relative to the distal end of the tubular shaft 337 of the retrieval device 338 to thereby close or contract the end effector. This mechanism of operation is similar to that described with respect to the rotation cap 286 and the spring 255 of the medical device 200 above.

Figure 18B:
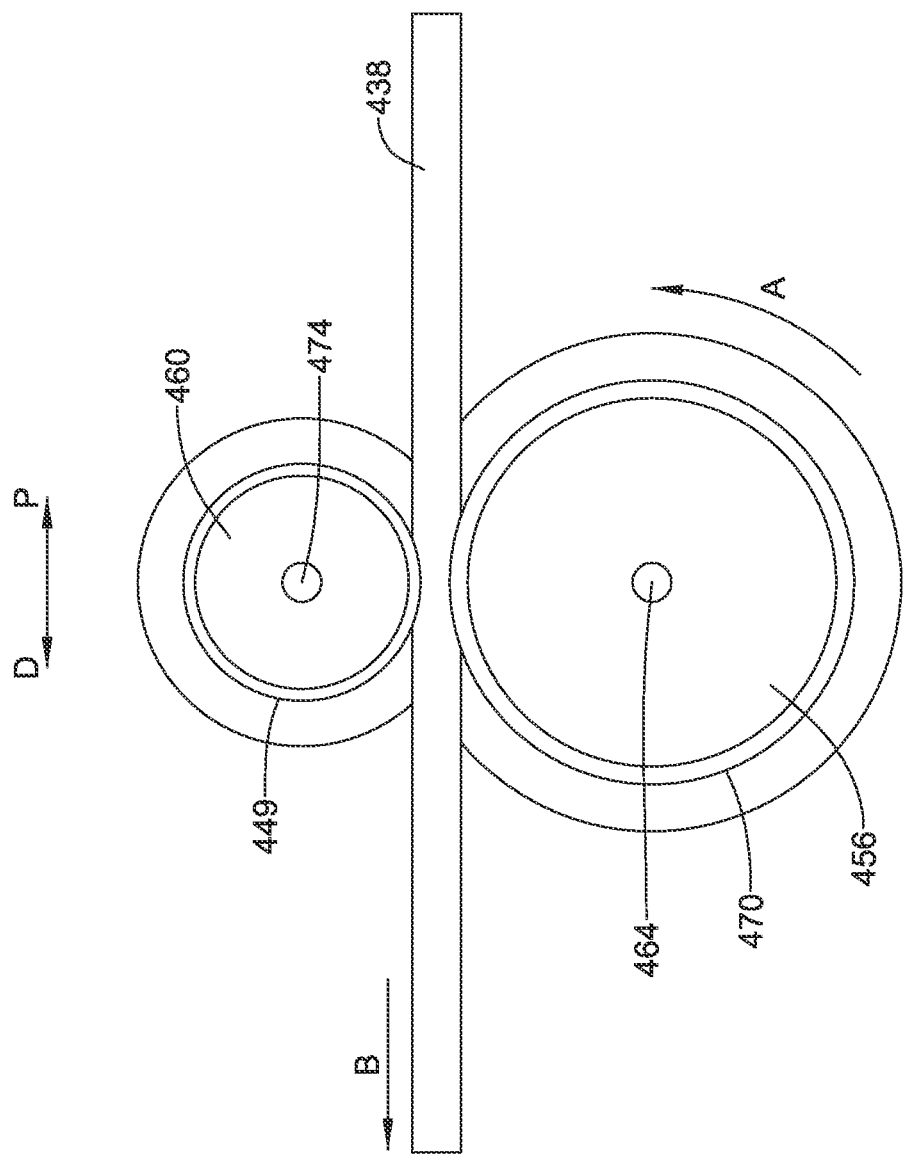
FIG. 18B is a side view of the shaft advancement mechanism of FIG. 18A.

Another embodiment of a shaft advancement device 434 is shown in FIGS. 18A and 18B. As with the other shaft advancement devices 34/134/234/334 disclosed herein, the shaft advancement device 434 may be removably or fixedly attached to the handle of a medical device. In many aspects, the operation of the shaft advancement device 434 may be similar to that of the other shaft advancement devices 34/134/234/334, with some alterations. As such, the features of the shaft advancement device 434 may be physically incorporated into the other shaft advancement devices 34/134/234/334, described above, if desired.

As shown in FIG. 18A, the shaft advancement device 434 may include a housing 462 that is attachable (removably or fixedly) to the handle of a medical device, such as the other medical devices described above. The shaft advancement device 434 may include a thumbwheel 456 coupled to the housing 462 via the extension of an axle 464 through an aperture of the thumbwheel 456. Accordingly, the thumbwheel 456 is rotationally coupled to the housing 462 via the axle 464 such that the thumbwheel 456 is permitted to rotate about the axis of the axle 464. Similar to the other thumbwheels above, the thumbwheel 456 may include a band 470 of material that extends circumferentially around the perimeter of the thumbwheel 456. The material that is used to construct the band of material 470 may be designed too generally include materials which provide grip when a user is manipulating the thumbwheel 456. For example, the band of material 470 may include rubber, silicone, nitrile butadiene rubber, thermoplastic elastomers, neoprene, other elastic materials, or similar materials.

When assembled, it can be appreciated that the thumbwheel 456 may be rotated around the axle 464 in ether a clockwise or counterclockwise direction. Further, as will be described in greater detail below, a physician may use their thumb (or another finger) of their hand grasping the handle of the medical device to manually rotate the thumbwheel 456. Unlike the embodiments described above, the shaft advancement device 434 may not include a separate drive wheel, instead, the shaft advancement device 434 may only include the thumbwheel 456, which also acts as a drive wheel, and a roller wheel 460.

The roller wheel 460 may be coupled to the housing 462 via an axle 474, which extends away from the surface of the housing 462. It can be appreciated that the roller wheel 460 may rotate in a clockwise direction or a counterclockwise direction around the axis of the axle 474. Additionally, FIG. 18A illustrates that the roller wheel 460 may include a band of material 449 extending circumferentially around its perimeter. The band of material 449 may be similar in form and function as the band of material 470 described above. The circumferential surface of the thumbwheel 456 may be placed adjacent to the circumferential surface of the roller wheel 460. For example, the roller wheel 460 may be in contact with the thumbwheel 456 (e.g., the band of material 470 of the thumbwheel 456 may directly contact the band of material 449 of the roller wheel 460), or a small gap may remain therebetween for placement of the elongate shaft 438 of a medical device (e.g., a retrieval device or laser fiber) therebetween.

FIG. 18B illustrates the mechanism by which the elongate shaft 438 is advanced (or retracted) into and out of the working channel of the elongate shaft of a medical device (e.g., an endoscope) via manipulation of the thumbwheel 456. Rotation of the thumbwheel 456 will cause rotation of the roller wheel 460 in a direction that is opposite to the rotation of the thumbwheel 456. For example, as shown in FIG. 18B, counterclockwise rotation (as viewed from the outer surface of the thumbwheel 456) of the thumbwheel 456 will cause a clockwise rotation of the roller wheel 460. With the elongate shaft 438 of a medical device positioned therebetween, counterclockwise rotation of the thumbwheel 456, shown by arrow A, will cause the elongate shaft 438 to be advanced distally, as shown by the arrow B. Likewise, clockwise rotation of the thumbwheel 456 will cause the elongate shaft 438 to be retracted proximally.

It can be appreciated that the ability of the thumbwheel 456 to translate the elongate shaft 438 relative to the first connection tube (described above) and the working channel of the elongate shaft of the endoscope (described above) is created via a compressive force imparted onto the elongate shaft 438 as it is sandwiched between the thumbwheel 456 and the roller wheel 460. It can be further appreciated that the thumbwheel 456 and the roller wheel 460 must be spaced apart from one another to permit the shaft advancement device 434 to sufficiently advance the elongate shaft 438 within the first connection tube and the working channel of the elongate shaft of the endoscope (described above) without slipping while also making the tactile feedback of the thumbwheel 456 comfortable for the user. In some examples, the roller wheel 460 may be attached to a spring such that the spacing between the thumbwheel 456 and the roller wheel 460 is adjustable for elongate shafts of medical devices having varying outer diameters.

As noted above, any of the shaft advancement devices disclosed herein may be configured with only a thumbwheel and a roller wheel, as described in association with FIGS. 18A-18B, if desired.

The materials that can be used for the various components of the examples disclosed herein may include those commonly associated with medical devices. For simplicity purposes, the following discussion refers to ureteroscope instruments and other components of a ureteroscope. However, this is not intended to limit the devices and methods described herein, as the discussion may be applied to other similar tubular members and/or components of tubular members or devices disclosed herein.

The medical device 10 and/or components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear-elastic" or "non-super-elastic" which, although may be similar in chemistry to conventional shape memory and super-elastic varieties, may exhibit distinct and useful mechanical properties. Linear-elastic and/or non-super-elastic nitinol may be distinguished from super-elastic nitinol in that the linear-elastic and/or non-super-elastic nitinol does not display a substantial "super-elastic plateau" or "flag region" in its stress/strain curve like super-elastic nitinol does. Instead, in the linear-elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super-elastic plateau and/or flag region that may be seen with super-elastic nitinol. Thus, for the purposes of this disclosure linear-elastic and/or non-super-elastic nitinol may also be termed "substantially" linear-elastic and/or non-super-elastic nitinol.

In some cases, linear-elastic and/or non-super-elastic nitinol may also be distinguishable from super-elastic nitinol in that linear-elastic and/or non-super-elastic nitinol may accept up to about 2-5% strain while remaining substantially elastic (e.g., before plastically deforming) whereas super-elastic nitinol may accept up to about 8% strain before plastically deforming. Both of these materials can be distinguished from other linear-elastic materials such as stainless steel (that can also be distinguished based on its composition), which may accept only about 0.2 to 0.44 percent strain before plastically deforming.

In some embodiments, the linear-elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear-elastic and/or non-super-elastic nickel-titanium alloy. The mechanical bending properties of such material may therefore be generally inert to the effect of temperature over this very broad range of temperature. In some embodiments, the mechanical bending properties of the linear-elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear-elastic and/or non-super-elastic nickel-titanium alloy maintains its linear-elastic and/or non-super-elastic characteristics and/or properties.

In some embodiments, the linear-elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a super-elastic alloy, for example a super-elastic nitinol can be used to achieve desired properties.

In at least some embodiments, a ureteroscope instrument and/or other portions of assembly may also be doped with, made of, or otherwise include a radiopaque material. Radiopaque materials are understood to be materials capable of producing a relatively bright image on a fluoroscopy screen or another imaging technique during a medical procedure. This relatively bright image aids the user of assembly in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of assembly to achieve the same result.

In some embodiments, a degree of Magnetic Resonance Imaging (MRI) compatibility is imparted into an example. For example, a ureteroscope instrument, or portions thereof, may be made of a material that does not substantially distort the image and create substantial artifacts (e.g., gaps in the image). Certain ferromagnetic materials, for example, may not be suitable because they may create artifacts in an MRI image. A ureteroscope instrument, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An actuation mechanism for an endoscope, comprising:
a housing configured to be attached to a handle of an endoscope;
a first thumbwheel coupled to the housing; and
a first connection tube having a proximal end coupled to the housing and a distal end configured to connect with an access port on the handle of the endoscope;
the first thumbwheel is configured such that rotation of the first thumbwheel causes longitudinal translation of a first elongated medical device through the first connection tube, out the distal end of the first connection tube, and into and through the working channel of the endoscope wherein the housing includes a channel extending from an outer surface of the housing into a portion of a wall of the housing, wherein the channel is configured to accept a proximal end of a tubular member of the first elongated medical device, and wherein the proximal end of the tubular member of the first elongated medical device is fixedly attached to the channel, and wherein the channel is configured to accept an elongate member of the first elongated medical device extending within a lumen of the tubular member of the first elongated medical device.

2. The actuation mechanism of claim 1, further comprising a first drive wheel coupled to the housing, the first thumbwheel engaging the first drive wheel, wherein rotation of the first thumbwheel is configured to cause rotation of the first drive wheel.

3. The actuation mechanism of claim 2, further comprising a first roller wheel coupled to the housing, wherein an outer circumferential surface of the first roller wheel is positioned adjacent to an outer circumferential surface of the first drive wheel such that the first elongated medical device may be positioned between the outer circumferential surface of the first roller wheel and the outer circumferential surface of the first drive wheel, and wherein rotation of the first thumbwheel is configured to cause rotation of the first drive wheel to move the first elongated medical device through the working channel of the endoscope.

4. The actuation mechanism of claim 3, wherein the first roller wheel and the first drive wheel are configured to cooperatively exert a compressive force on the first elongated medical device to frictionally engage the first elongated medical device therebetween.

5. The actuation mechanism of claim 4, wherein the first thumbwheel includes a circumferential surface, and wherein each of the first thumbwheel, the first drive wheel and the first roller wheel have respective bands of material extending therearound.

6. The actuation mechanism of claim 4, wherein the housing includes an inner housing and an outer housing, wherein the first thumbwheel, the first drive wheel and the first roller wheel are positioned between the inner housing and the outer housing.

7. The actuation mechanism of claim 3, further comprising a second thumbwheel coupled to the housing, a second drive wheel coupled to the housing and a second roller wheel coupled to the housing, and wherein the second thumbwheel engages the second drive wheel, and wherein rotation of the second thumbwheel is configured to cause longitudinal translation of a second elongated medical device through a working channel of the endoscope.

8. The actuation mechanism of claim 2, wherein the first thumbwheel includes a first diameter and the first drive wheel includes a second diameter, and
wherein the second diameter is less than the first diameter.

9. The actuation mechanism of claim 1, further comprising a first roller wheel coupled to the housing, wherein an outer circumferential surface of the first roller wheel is positioned adjacent to an outer circumferential surface of the first thumbwheel such that the first elongated medical device may be positioned between the outer circumferential surface of the first roller wheel and the outer circumferential surface of the first thumbwheel, and wherein rotation of the first thumbwheel is configured to cause rotation of the first roller wheel to move the first elongated medical device through the working channel of the endoscope.

10. The actuation mechanism of claim 1, further comprising a rotation cap coupled to the housing, and wherein a proximal end of the elongate member is attached to the rotation cap, and wherein rotation of the rotation cap is configured to move the elongate member within the lumen of the tubular member of the first elongated medical device.

11. An endoscopic medical device, comprising:
a handle having a proximal end region and a distal end region;
an elongate shaft coupled to the distal end region of the handle and extending distally therefrom;
an actuation assembly coupled to the proximal end region of the handle, wherein the actuation assembly includes:
a housing;
a first thumbwheel coupled to the housing;
a second thumbwheel coupled to the housing;
a first connection tube having a proximal end coupled to the housing and a distal end configured to connect with an access port of the handle;
a second connection tube having a proximal end coupled to the housing and the second connection tube having a a distal end configured to connect with the access port of the handle, where the first and second connection tubes are different structures;
the first thumbwheel is configured such that rotation of the first thumbwheel causes a first elongated medical device to translate through the first connection tube, out the distal end of the first connection tube and into and through the elongate shaft;
the second thumbwheel is configured such that rotation of the second thumbwheel causes a second medical device to translate through the second connection tube, out the distal end of the second connection tube and into and through the elongate shaft wherein the actuation assembly further includes a first drive wheel and a first roller wheel coupled to the housing, the first drive wheel configured to be rotated by the first thumbwheel, and
wherein the actuation assembly further includes and a second drive wheel and a second roller wheel coupled to the housing, the second drive wheel configured to be rotated by the second thumbwheel, and wherein the first drive wheel and the first roller wheel are configured to cooperatively exert a force on the first medical device positioned therebetween, and wherein the second drive wheel and the second roller wheel are configured to cooperatively exert a force on the second medical device positioned therebetween.

12. The endoscopic medical device of claim 11, wherein the rotation of the first thumbwheel to translate the first medical device occurs independently of the rotation of the second thumbwheel to translate the second medical device.

13. The endoscopic medical device of claim 11, wherein rotation of the first thumbwheel is configured to rotate the first drive wheel and the first roller wheel in opposite rotational directions to translate the first elongated medical device through the elongate shaft, and
wherein rotation of the second thumbwheel is configured to rotate the second drive wheel and the second roller wheel in opposite rotational directions to translate the second elongated medical device through the elongate shaft.

14. The endoscopic medical device of claim 11, wherein the first thumbwheel includes a first diameter and the first drive wheel includes a second diameter, and
wherein the second diameter is less than the first diameter.

* * * * *